United States Patent

Miyata

[11] Patent Number: 6,082,105
[45] Date of Patent: Jul. 4, 2000

[54] DRIVE DEVICE FOR MEDICAL APPLIANCES

[75] Inventor: Shinichi Miyata, Tokyo, Japan

[73] Assignee: Nippon Zeon Co., Ltd., Tokyo, Japan

[21] Appl. No.: 09/091,365

[22] PCT Filed: Nov. 20, 1996

[86] PCT No.: PCT/JP96/03402

§ 371 Date: May 22, 1998

§ 102(e) Date: May 22, 1998

[87] PCT Pub. No.: WO97/18843

PCT Pub. Date: May 29, 1997

[30] Foreign Application Priority Data

Nov. 21, 1995 [JP] Japan ................................. 7-302493
Dec. 28, 1995 [JP] Japan ................................. 7-342522

[51] Int. Cl.[7] ............................................. F16D 31/02
[52] U.S. Cl. ............................................................. 60/410
[58] Field of Search ........................... 60/407, 409, 410, 60/411, 412, 415, 416, 418; 600/17, 18

[56] References Cited

U.S. PATENT DOCUMENTS

| | | | |
|---|---|---|---|
| 3,698,381 | 10/1972 | Federico et al. | 600/17 |
| 3,720,199 | 3/1973 | Rishton et al. | 600/18 |
| 3,791,374 | 2/1974 | Guarino | 600/17 |
| 4,016,871 | 4/1977 | Schiff | 600/18 X |
| 4,787,368 | 11/1988 | Kageyama | 600/18 |
| 4,794,910 | 1/1989 | Mushika | 600/18 |
| 4,796,606 | 1/1989 | Mushika | 600/18 |
| 4,832,005 | 5/1989 | Takamiya et al. | 600/18 |
| 4,942,735 | 7/1990 | Mushika et al. | 60/416 |
| 4,969,866 | 11/1990 | Inagaki | 600/18 |
| 4,974,774 | 12/1990 | Nakagawa et al. | 600/18 |
| 5,158,529 | 10/1992 | Kanai | 600/18 |
| 5,169,379 | 12/1992 | Freed et al. | 600/18 |
| 5,217,429 | 6/1993 | Kanai | 600/18 |
| 5,217,430 | 6/1993 | Mushika | 600/18 |

FOREIGN PATENT DOCUMENTS

| | | |
|---|---|---|
| 58-124453 | 7/1983 | Japan . |
| 60-106461 | 6/1985 | Japan . |
| 62-172963 | 7/1987 | Japan . |
| 2-131770 | 5/1990 | Japan . |
| 3-210272 | 9/1991 | Japan . |

*Primary Examiner*—John E. Ryznic
*Attorney, Agent, or Firm*—Armstrong, Westerman Hattori, McLeland & Naughton

[57] ABSTRACT

A medical-appliance driving apparatus is provided. The driving apparatus includes a first pressure sensor, which detects the inside pressure of a first positive pressure tank, and a second pressure sensor, which detects the inside pressure of a second negative pressure tank. A controller calculates the mean value of the pressure data detected by the first and second pressure sensors and if the mean value is greater than the predetermined mean value, a first valve is opened for a predetermined time. If the mean value is smaller than the predetermined mean value, then a second valve is opened for a predetermined time. The controller also calculates the pressure difference between the pressure data detected by the first and second sensors. If the pressure difference is greater than the predetermined difference value, the output level of a pump is lowered. If the pressure difference is smaller than the predetermined difference value, then the output level of the pump is raised. In this arrangement, the positive pressure and the negative pressure generated at the output ports of a single pump are kept in desired ranges and, as a result, the energy efficiency is improved.

16 Claims, 10 Drawing Sheets

DRIVE DEVICE FOR MEDICAL APPLIANCES

FIELD OF THE INVENTION

This invention relates to a driving apparatus for driving medical appliances, such as an artificial heart and an intra-aorta balloon pump (IABP), by alternately outputting positive pressure and negative pressure.

BACKGROUND OF THE INVENTION

Balloon catheters for IABP are often used in medical treatment of heart diseases. In the treatment, a balloon catheter is inserted into the artery near the heart of the patient, and the balloon is inflated and deflated in accordance with the heart beat of the patient in order to assist or activate the cardiac function. Japanese Patent Application Laid-open No. 60-106464 (hereinafter "JP '464") discloses a medical-purpose driving apparatus for inflating and deflating such balloons.

The driving apparatus disclosed in JP '464 has a primary tube line and a secondary tube line, which are separated from each other by a pressure-transfer isolator (simply called an isolator, or generally named a volume limiting device (VLD)). A change of pressure occurring in the primary tube line is transferred to the secondary tube line, and the resultant pressure change occurring in the secondary tube line inflates and deflates the balloon. The reason why the primary and secondary tube lines are separated is that different kinds of fluid gas are used in these two lines, namely, one as a driving medium for actually driving the balloon, the other as a pressure source for generating positive pressure and negative pressure. This is required to improve the response of inflation/deflation of the balloon and, at the same time, to generate necessary pressure at low cost. The pressure-transfer isolator is located between the pressure source and the balloon in order to prevent excessive gas from flowing into the balloon when the balloon is inflated.

In this Intra Aortic balloon catheter, helium gas, which has a small mass and a high response ability, is preferably used as the fluid gas filled in the secondary tube line. In this case, the helium gas functions as driving shuttle gas. Prior to filling the balloon and the secondary tube line with the helium gas, the balloon and the secondary tube line are evacuated. The pressure of helium gas to be filled is up to pressure near the atmospheric pressure or lower than that pressure. Filling pressure up to 10 mm Hg higher than the atmospheric pressure is acceptable, so that the deflation speed of the balloon can be increased, and the response to high heart rate is improved. It can also reduce the load on the heart muscle.

In the conventional technique, the primary tube line consists of a positive pressure line and a negative pressure line, and the positive and negative pressures are alternately transferred to the pressure-transfer isolator by means of a valve. The positive pressure line has a positive-pressure generating pump and a positive pressure tank, while the negative pressure line has a negative-pressure generating pump and a negative pressure tank. In other words, in the conventional method, positive pressure and negative pressure are generated by separate pressure sources.

Another type of driving apparatus for medical appliances is disclosed in Japanese Patent Application Laid-open No. 60-116366 (hereinafter "JP '366"). The driving apparatus of JP '366 uses a compressor as a positive-pressure generator, and a vacuum pump as a negative-pressure generator. The output ports of the respective pressure generators are connected to open/close valves. The output ports of the valves are connected to, for example, an artificial heart, which is driven by positive and negative pressure supplied through the valves.

However, providing two separate pressure generators is undesirable from the viewpoints of electric power consumption and the weight of the apparatus. In order to overcome this drawback, Japanese Patent Publication (after examination) No. 3-28595 (hereinafter "JP '595") and Japanese Patent Publication No. 4-61661 (hereinafter "JP '661") propose to use a single pressure generator having an input port, at which negative pressure is generated, and an output port, at which positive pressure is generated. The single pressure generator is used to generate positive and negative pressure to drive the balloon catheter.

The total weights of the driving apparatuses disclosed in both JP '595 and JP '661 are reduced, however, have problems in energy efficiency.

In JP '595, when the pressure of the positive pressure tank exceeds a predetermined level, the excessive pressure is released in the atmosphere using an solenoid valve connected to the output port of the pressure generator. This structure requires a check valve between the positive pressure tank and the solenoid valve in order to prevent too much pressure from being released. Similarly, when the negative pressure is reduced below a predetermined value, the input port of the pressure generator is opened to the atmosphere through another solenoid valve, and another check valve is required between the negative pressure tank and the input port. The energy efficiency of the apparatus apparently becomes worse when the pump (i.e., the pressure generator) is driven under condition beyond the predetermined pressure, because the input and output ports of the pump are opened to the atmosphere to regulate the pressures to the desired levels. During the period that the input or output ports opens, the pump is generating a useless pressure that does not contribute to driving the balloon. If a pump having a comparative low output is used in order to shorten the period of time that the input or output ports open, the pump cannot supply sufficient positive pressure when the heart beat rate of the patient has increased. To avoid such a situation, it is necessary to use a pump having an excessive power and to discard a portion of its output.

In JP '661, the driving apparatus has a switching valve between the positive side of the pressure generator and the positive pressure tank. This valve is open to connect the positive pressure tank and the positive side of the pressure generator until the pressure of the positive pressure tank reaches a predetermined value. When the pressure of the positive pressure tank has exceeded the predetermined value, the valve shuts off the connection and, at the same time, opens the positive side to the atmosphere.

Another switching valve is provided between the negative side of the pressure generator and the negative pressure tank. The negative side of the pressure generator is connected to the negative pressure tank via this valve until the negative pressure of the tank reaches a predetermined value. When the pressure of the negative pressure tank has lowered below the predetermined value, the valve shuts off the connection and opens the positive side to the atmosphere.

Similar to JP '595, the energy efficiency worsens when one or both of the ports are opened to the atmosphere. In either JP '595 or JP '661, the energy efficiency of the driving apparatus is likely to easily drop if the object to be driven is small, or if the heart beat rate is low (or if the inflation/deflation cycle is long).

In other words, in accordance with the conventional apparatuses, the energy efficiency becomes worse, especially when only a small amount of work is required. Low energy efficiency causes a high power consumption, so that the power source capacity must be kept large even though the number of pumps is reduced.

Since the medical-appliance driving apparatus is carried to many places inside and outside of the hospital, it is desirable for the built-in power source capacity to be made as small as possible. However, the conventional apparatuses require high power of the built-in power source because of high power consumption.

Japanese Patent Application Laid-Open No. 5-261148 (hereinafter "JP '148") also discloses a driving apparatus that has a similar drawback. A portion of the output from the pressure generator is abandoned, and the energy efficiency of this apparatus is not good enough.

Actually, it is a great advantage for a driving apparatus, especially those used for an artificial heart or an intra-aorta balloon, to reduce the number of pumps (i.e., pressure generators) from two to one because the weight and the number of components can be reduced.

However, in the conventional driving apparatuses, the positive and negative pressure applied to the output ports must be kept within a certain range. For this reason, a larger sized pump is used in accordance with high heart beat rate, while a portion of the generated pressure is abandoned in the normal condition. Thus, the low energy efficiency of the conventional apparatus can not be avoided.

In the conventional medical-appliance driving apparatuses, the secondary tube line and the balloon must be evacuated before they are filled with shuttle gas (e.g., helium gas). This requires an additional evacuation pump and, accordingly, causes the conventional driving apparatuses for medical appliances to become large and heavy with a number of components.

By the way, IABP driving apparatuses or AH (artificial heart) driving apparatuses generally have an alarm system, for detecting a malfunction or a defect of the balloon membrane, or other devices under various circumstances. However, for example, in order to find a very small pin hole in the balloon membrane, which may cause frequent supply of helium gas, not only the operation information at the alarm point of time, but also several tens of hours of past data, including the information about the normal operation and the information immediately before the alarm, are required. Whenever an alarm occurs, some of the conventional driving apparatuses (e.g., KAAT manufactured by Kontron Inc.) output, the blood pressure and the electrocardiograph of the patient, the balloon activation waveform, and the reason for the alarm on the printed papers by printer. This type of driving apparatus also outputs these data on the printed papers when the patient's condition changes for the worse with, for example, a disorder in the electrocardiograph, even if the system itself is normally working. It is confusing to have to distinguish between the malfunction of the system and the change of the patient's condition. In addition, a great volume of paper is consumed wastefully.

Of course, it has been proposed to connect the medical-appliance driving apparatus to a personal computer via a parallel interface and transmit the data, including the operational state of the system, to the personal computer.

However, the power source of a general-use personal computer does not have a sufficient insulating ability, and it is likely to cause leakage current to increase in the patient's body if such a general-use personal computer is connected directly to the driving apparatus having an electrocardiograph input unit. Accordingly, it becomes necessary to insulate the interface to the personal computer using an optocoupler or an optoisolator. Because multi-channel parallel interfaces are not preferable with respect to cost and operation, an attempt is being made to connect the medical-appliance driving apparatus to the personal computer using a serial interface.

Unfortunately, it takes several tens of minutes for the serial interface to transfer the past data stored in the memory of the driving apparatus to the personal computer, depending on the amount of data stored. In practice, if a problem is detected in the apparatus, the stored data, such as the past and current operation data, must be transferred to the computer as soon as possible for analysis of the problem because any adverse influence to the patient must be avoided. Although a parallel interface can improve the data transmit speed, it must be insulated from the personal computer, which requires additional cost and components.

SUMMARY OF THE INVENTION

Therefore, it is a first object of the present invention to provide a medical-appliance driving apparatus using a single pump with improved energy efficiency, while the positive pressure and the negative pressure generated in the input port and the output port of the pump are kept in desired ranges.

It is a second object of the present invention to provide a compact and reliable medical-appliance driving apparatus by reducing the weight and the number of components, while keeping reliable performance.

It is a third object of the present invention to provide a medical-appliance driving apparatus having a good insulating ability, which can promptly transfer the stored data to a personal computer for data analysis.

First Aspect of the Invention

In order to achieve the above-described first object of the present invention, a medical-appliance driving apparatus has a pressure generator for generating a positive pressure and a negative pressure simultaneously. The pressure generator has a positive-pressure output port and a negative-pressure output port. A first pressure tank is connected to the positive-pressure output port, and the pressure inside the first pressure tank is detected by a first pressure sensor. A first opening/closing valve is provided so that the input port of the valve is connected to the first pressure tank or the tube in front of or behind the first pressure tank, and so that the output port of the valve is open to the atmosphere. A second pressure tank is connected to the negative-pressure output port of the pressure generator, and the pressure inside the second pressure tank is detected by a second pressure sensor. A second opening/closing valve is provided so that the input port of the second valve is connected to the second pressure tank or the tube in front of or behind the second pressure tank, and so that the output port of the second valve is open to the atmosphere. A pressure switching means is connected to both the first and second pressure tanks. The switching means switches the pressures of the first and second pressure tanks and supplies one of the pressures to the output port of the switching means. A controller controls the first and second opening/closing valves so that the detection data of the first pressure sensor substantially equal to or more than first predetermined data, and that the detection data of the second pressure sensor substantially equal to or less than second predetermined data.

Preferably, the controller calculates the mean value of the detection data detected by the first and second pressure sensors. If the calculated mean value is greater than the predetermined mean value, the controller causes the first opening/closing valve to open for predetermined duration. If the calculated mean value is smaller than the predetermined mean value, the controller causes the second opening/ closing valve to open for predetermined duration. Note that the mean data shows the intermediate value between the pressure data (normally positive number) of the first pressure tank and the pressure data (normally negative number) of the second pressure tank.

Preferably, the controller also calculates a pressure difference between the detection data detected by the first and second pressure sensors. If the pressure difference is greater than the predetermined difference value, the controller causes the pressure generator to decrease its output level. If the pressure difference is smaller than the predetermined difference value, the controller causes the pressure generator to increase its output level.

The driving apparatus of the present invention is used to drive medical appliances, such as an artificial heart and an intra aorta balloon, which require positive pressure and negative pressure alternately.

When the driving apparatus is used for an artificial heart, the pump (i.e., the pressure generator), the positive and negative pressure tanks, the pressure switching mechanism, the path from the output port thereof, and the to blood pump bladder form a sealed circuit. If the driving apparatus is used for an intra aorta balloon, then the pump, the positive and negative pressure tanks, the pressure switching mechanism, and the partition (or the insulator) for driving the helium gas or carbon dioxide gas form a sealed circuit.

Air is generally used as the fluid flowing through the sealed circuit. However, other compressible gases can also be used. The compressible gas, or air, generates heat during the irreversible compression process, while it absorbs heat during the irreversible expansion process when the gas passes through the switching mechanism from the negative tank. Mechanical loss in the pump also causes heat generation, which further causes the inside temperature to change.

Therefore, if the sealed circuit is kept closed, either the positive pressure or the negative pressure will be out of the preferable range depending on the condition in the circuit. For example, if the gas temperature in the system rises, the positive pressure becomes too high, and the negative pressure approaches the atmospheric pressure.

In order to avoid such a situation, a portion of the gas should be discharged to the atmosphere from the sealed circuit at a certain place where the pressure is always kept higher than the atmospheric pressure, for example, at the positive tank or the tube line near the tank. A solenoid valve may be used to discharge the gas. One port of the solenoid valve is opened to the atmosphere, and the other port of the valve is connected to the discharge point. The valve may be opened repeatedly for predetermined duration.

If the gas temperature of the system drops due to the fluctuation of the operating condition, the negative pressure becomes too low and the positive pressure approaches the atmospheric pressure. In addition, other than the temperature change, gas leakage also causes the amount of gas within the system to become either excessive or insufficient. If leakage occurs in a tube line where the internal pressure is lower than the atmospheric pressure, the gas in the system increases excessively. If there is leakage in a high-pressure tube line, then the gas flowing in the sealed circuit becomes insufficient.

In order to supply the air to the system, a place where the internal pressure is always lower than the atmospheric pressure may be connected to the atmosphere by means of an solenoid valve. One end of the solenoid valve is open to the atmosphere, and the other end of the solenoid valve is connected to the negative tank or the tube near this tank. By opening the solenoid valve repeatedly, air is supplied to the sealed system.

The controller calculates the mean value between the actually detected pressure values of both pressure tanks. If the calculated mean value is greater than the predetermined mean value between the preset pressure data of the tanks, the gas in the sealed circuit is discharged, and if the calculated mean value is smaller than the preset mean value, then the gas is supplied to the sealed circuit.

Under this control operation, the mean value of the detected pressure data becomes substantially constant. However, if each of the absolute value of the detected pressure data of both the positive pressure tank and the negative pressure tank is greater than the predetermined data, then both of the tank pressure can not reach the predetermined pressure data respectively, even if the mean value is the same as the predetermined mean value. In such a case, the driving condition of the pump (i.e., the pressure generator) is changed in order to bring the detected pressure data of the positive and negative pressure tanks to the corresponding predetermined data respectively.

In particular, the difference between the detected pressure data of the positive and negative pressure tanks is compared with the reference pressure difference between the preset pressure data of the positive and negative pressure tanks. If the detected pressure difference is greater than the reference pressure difference, the output of the pump is lowered. If the detected pressure difference is smaller than the reference pressure difference, the output level of the pump is raised.

In controlling the pump output, if the pump (e.g., a rotary pump, a diaphragm pump, a piston pump, etc.) has an alternating current (AC) induction motor, the output level of the pump can be lowered by decreasing the power source frequency or the amplitude of the power source voltage supplied to the (AC induction) motor. For a linear piston pump using an AC power source, the output level can be lowered by the same method. If the motor of the pump, such as a rotary pump, a diaphragm pump, a piston pump, etc., uses a servo-motor, the output level of the pump can be controlled by adjusting the target rotation speed. If the pump has a DC motor, the output level of the pump is controlled by regulating the PWM (pulse width modulation) of the motor power source or adjusting the exciting voltage/ current.

In the pressure control based on the mean value between the detected pressure data of the positive and negative pressure tanks, the tank pressure is controlled so that the mean value always lies within a predetermined range. In to this control, it is not necessary to open the solenoid valve for every heart beat to release the gas. In other words, wasteful emission of the positive and negative pressure of the tanks, which are produced as a result of the work done by the pump to the internal gas flow using the input energy, can be eliminated.

This is a significant advantage over the conventional driving apparatus which has a poor energy efficiency because of the fact that whenever the positive or negative pressure of each tank is out of the predetermined range, the tank is disconnected from the pump which keeps on working on the gas fluid.

In the present invention, the output level of the pump itself is controlled so as not to abandon the pump output into the atmosphere, whereby the energy efficiency of the driving apparatus is greatly improved.

The input and output of the gas flowing in the sealed circuit is kept at a minimum, while a waste of work done by the pump can be effectively avoided. The controlled pump output can reduce the power consumption and improve the energy efficiency.

Second Aspect of the Invention

In the second aspect of the present invention, a medical-appliance driving apparatus has a primary pressure generator for simultaneously generating positive pressure and negative pressure, a primary tube line having a positive pressure line connected to the positive-pressure output port of the primary pressure generator, and a negative pressure line connected to the negative-pressure output port of the primary pressure generator. The driving apparatus also has a secondary pressure generator which comprises a pressureto transfer isolator. The pressure isolator has a first chamber, into which the positive pressure and the negative pressure generated by the primary pressure generator are alternately introduced through the primary tube line, and a second chamber which is isolated from the first chamber, and to which at least a portion of the pressure of the first chamber is transferred. A secondary tube line is connected to the second chamber of the secondary pressure generator. The other end of the secondary tube line is connected to a device that is to be inflated and deflated by the supplied pressures. A gas substitution tube line is connected between the secondary tube line and the negative pressure line of the primary tube line in a manner to allow and reject gas flow between the secondary tube line and the negative pressure line. A valve for controlling the gas flow between the secondary tube line and the negative pressure line is equipped with the gas substitution line.

Preferably, a moisture remover is also equipped with the gas substitution line in order to remove the moisture contained in the gas flowing through this tube line.

The moisture remover may be designed so that positive pressure can be supplied from the positive pressure line of the primary tube line to the moisture remover at a desired time. The supplied positive pressure forcibly removes the condensed liquid.

In this driving apparatus, any type of pressure generator can be used. For example, a diaphragm pump, a piston pump, a linear piston pump, a rotary vane pump, or similar can be used. Among them, a diaphragm pump and a piston pump are preferable because a highly evacuated state can be achieved at a low flow rate.

In this specification, the primary and secondary tube lines include any tubes or hoses, and tanks connected to those tubes or hoses.

A single pressure generator (such as a pump) is used to generate positive pressure, which is to be applied to the positive pressure line, and a negative pressure which is to be applied to the negative pressure line. This pressure generator is also used to discharge the gas remaining in the secondary tube line prior to introducing shuttle gas into the secondary tube line. Consequently, the driving apparatus becomes compact and light with a decreased number of components, while the reliability of the apparatus is improved.

The moisture remover placed in the gas substitution tube line can prevent condensed water from entering the pump (i.e., the pressure generator) and the primary tube line is connected to the pump when the secondary tube line is evacuated in order to replace the gas remaining in the secondary tube line with shuttle gas. If the water gets into the pump and the primary tube line, the pump may become dysfunctional due to overload.

Examples of the moisture remover include a water trap having a simple drain and a dehumidify agent. When using a water trap with a simple drain, the apparatus may be designed so that a positive pressure is applied to the water trap from the positive pressure line of the primary tube line at an appropriate time in order to forcibly remove the condensed liquid. A dehumidify agent or a water-absorbing polymer can also prevent water from entering the primary tube line. However, such a water-absorbing substance must be changed at an appropriate time.

Air is generally used as the fluid flowing through the primary tube line. However, other compressible gases can also be used. Compressible gas, including air, generates heat during the irreversible compression process, while it absorbs heat during the irreversible expansion process when the gas passes through the switching mechanism from the negative tank. Mechanical loss in the pump also causes heat generation, which further causes the gas temperature to change.

Therefore, if the tube line is kept sealed, either the positive pressure or the negative pressure will be out of the preferable range. For example, if the gas temperature in the system rises, the positive pressure becomes too high, and the negative pressure approaches atmospheric pressure.

In order to avoid such a situation, a portion of the gas is discharged from the sealed line at a certain place where the pressure is always kept higher than the atmospheric pressure, for example, at the positive tank or the tube line near the tank. A solenoid valve may be used to discharge the gas. One side of the solenoid valve is opened to the atmosphere, and the other side of the valve is connected to the discharge point. The valve may be opened repeatedly for a predetermined time.

If the gas temperature of the system drops due to the fluctuation of the operating condition, the negative pressure becomes too low and the positive pressure approaches atmospheric pressure. In addition, other than the temperature change, gas leakage also causes the amount of gas within the system to become excessive or insufficient. If leakage occurs in a tube line where the internal pressure is lower than the atmospheric pressure, the gas in the system increases excessively. If there is leakage in a high-pressure tube line, then the gas flowing in the sealed circuit becomes insufficient.

In order to supply air to the system, a place where the internal pressure is always lower than the atmospheric pressure may be connected to the atmosphere by means of an solenoid valve. One end of the solenoid valve is open to the atmosphere, and the other end of the solenoid valve is connected to the negative tank or the tube near this tank. By opening the solenoid valve repeatedly, air is supplied to the sealed line.

Although there is no limitation to the shuttle gas supplied into the secondary tube line, helium gas is preferably used because of its small mass and small flow-resistance.

Third Aspect of the Invention

In the third aspect of the present invention, an apparatus for driving medical appliances that directly contact with the patient's body is provided. This driving apparatus comprises a driving state monitor for monitoring the driving state of the driving apparatus, and a data storage medium, attached to the driving apparatus in a detachable manner, for storing the data representing the driving state monitored by the driving state monitor.

Preferably, the driving state monitor samples the driving state of the apparatus for a predetermined period of time at a predetermined time interval. The sampled data is stored in the data storage medium in time series. If the memory capacity of the data storage medium is full, the current data is written over the oldest data.

When the driving state monitor receives a signal representing the notice that the data storage medium is going to be detached from the driving apparatus, the driving state monitor stops data transfer to the data storage medium, and starts storing the data in the built-in memory.

The driving state monitor is, for example, a CPU for controlling the overall operations of the driving apparatus. In the preferred embodiment, the driving state monitor samples the data for several seconds to several tens of seconds at a time interval of several minutes to several tens of minutes in order to monitor the driving state of the apparatus, as well as the blood pressure and the electrocardiograph of the patient which are required to determined the driving state of the apparatus. The monitoring result is stored in the data storage medium. When an alarm sounds, the driving pulses for several seconds before and after the alarm, and the possible factors that caused the alarm are stored in the data storage medium.

Any type of data storage media can be used as long as the data storage media are connected to and disconnected from the driving apparatus, and as long as the data storage media can maintain the data even after the disconnection. Examples of the data storage media include a shock-resistant magnetic memory, an overwritable optical disk, and a memory card. Among the data storage media listed, a memory card is preferable from the viewpoints of cost and portability because memory cards are standardized, based on, for example, the PCMCIA standard, and because recent notebook-type personal computers generally have an interface for a memory card. A recent notebook-type computer is light with a weight of several kilograms or less, and is easily brought into the medical treatment room. The operator simply removes the memory card from the driving apparatus and inserts it into the personal computer to quickly analyze the driving state before and after the alarm.

Since it is not necessary to connect the personal computer directly to the driving apparatus for the data analysis, there is no leak current flowing from the personal computer into the patient's body. The driving state data can be transferred to an expert (or a data analyst) through, for example, a public telephone line, using a known modem.

If a memory card is used as the data storage medium, the driving apparatus does not have to be furnished with a special interface because such a memory card can be a part of the memory space of the CPU, similar to other built-in (fixed) memories.

It takes several micro-seconds ($\mu$s) to several millisecond (ms) for an overwritable E2 PROM or a flash memory to write 17-word data. However, a battery-back upped RAM can write the same amount of data much faster, in several tens to several hundreds of nanoseconds. The battery-back upped RAM stores the data as a group of variables in the memory without requiring a special writing routine in its program. To avoid the case where the data amount exceeds the memory capacity of the data storage medium, the data may be stored as a ring buffer structure in the medium. The current data is successively written over the oldest data in time series, so that the most recent data can always be stored in accordance with the ring buffer structure.

Furthermore, in order to avoid the situation where the data storage medium is removed from the driving apparatus during the data writing process, which influences the CPU of the driving apparatus adversely and may destroy a part of the data stored in the storage medium, a removal notice switch is provided to the driving apparatus. The removal notice switch may be of a contact type or a non-contact type. When a removal notice signal is input to the CPU, the CPU stops transferring the data to the data storage medium and, instead, starts storing the data in the built-in memory. However, if a PCMCIA standard (Release 2.1) memory card is used as the data storage medium, it can be removed from the connector in the active line without causing any problems in the hardware.

Any data can be stored in the data storage medium, other than the driving state. For example, if the driving apparatus is used for a catheter of IABP, the operation time of the driving apparatus, the number of operations of the pressure-switching solenoid valve and the gas-supply solenoid valve, the state of charge/discharge of the battery, operation time of the positive and negative pumps, the power source voltage of each component, the internal temperature of the driving apparatus, and other maintenance data can be stored in the data storage medium, together with the blood pressure, the electrocardiograph, the waveform of the balloon driving pressure, and the alarm data.

The maintenance data stored in the data storage medium helps the inspection of the driving apparatus. For example, the memory card removed from the driving apparatus may be sent to the manufacturer or the service center of the driving apparatus for regular inspection of the driving apparatus.

BRIEF DESCRIPTION OF THE DRAWINGS

The present invention will be described in more detail based on the preferred embodiments with reference to the attached drawings, wherein.

PREFERRED EMBODIMENT OF THE INVENTION

The preferred embodiments of the present invention will now be described with reference to the attached drawings.

(First Embodiment)

Figure 1:
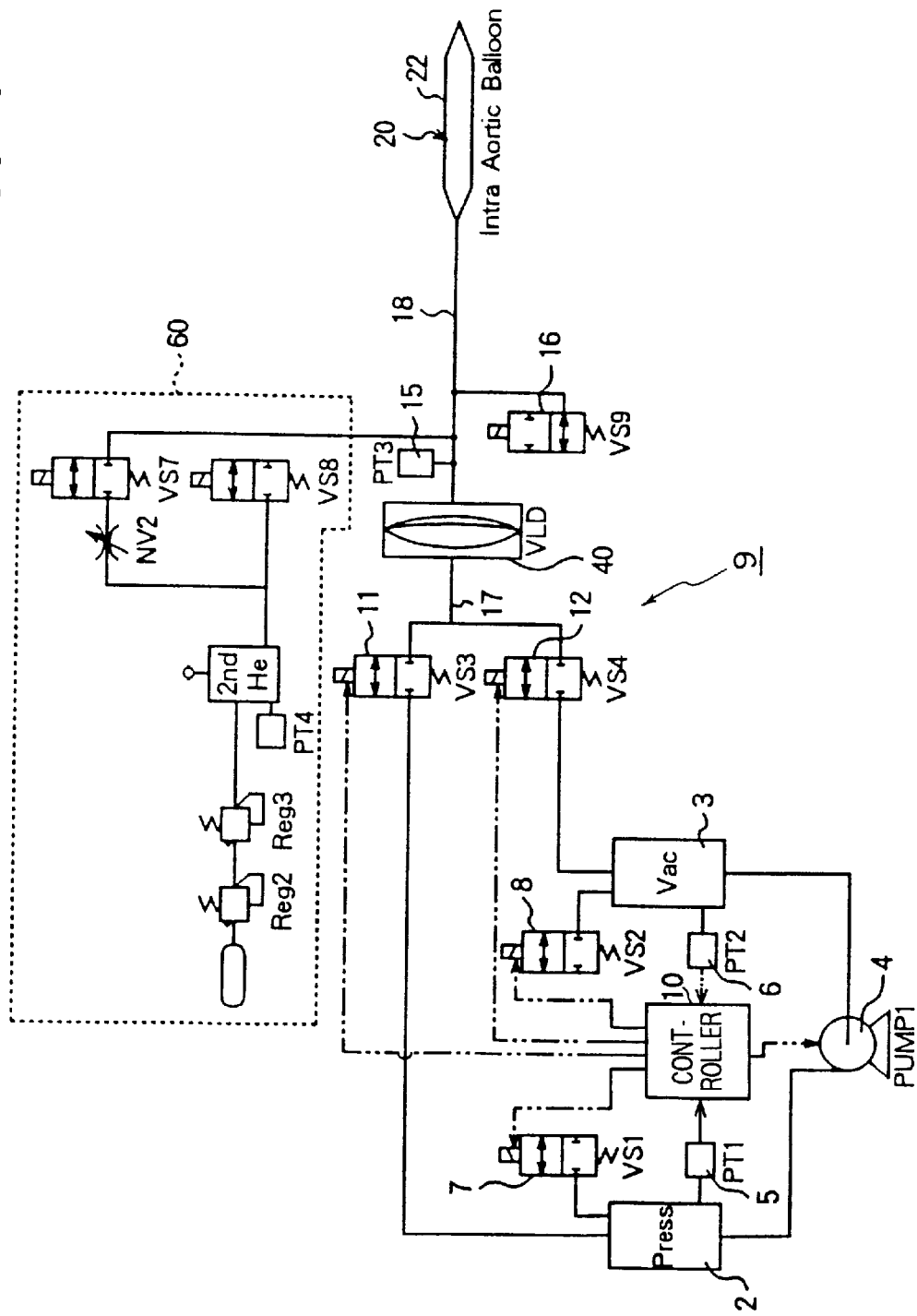
FIG. 1 is a schematic diagram of the medical-appliance driving apparatus according to a first embodiment of the present invention.

The driving apparatus shown in FIG. 1 is used to expand and deflate the balloon 22 of the balloon catheter 20 for IABP.

Prior to describing the medical-appliance driving apparatus of the first embodiment, the balloon catheter 20 for IABP will be explained.

Figure 4:
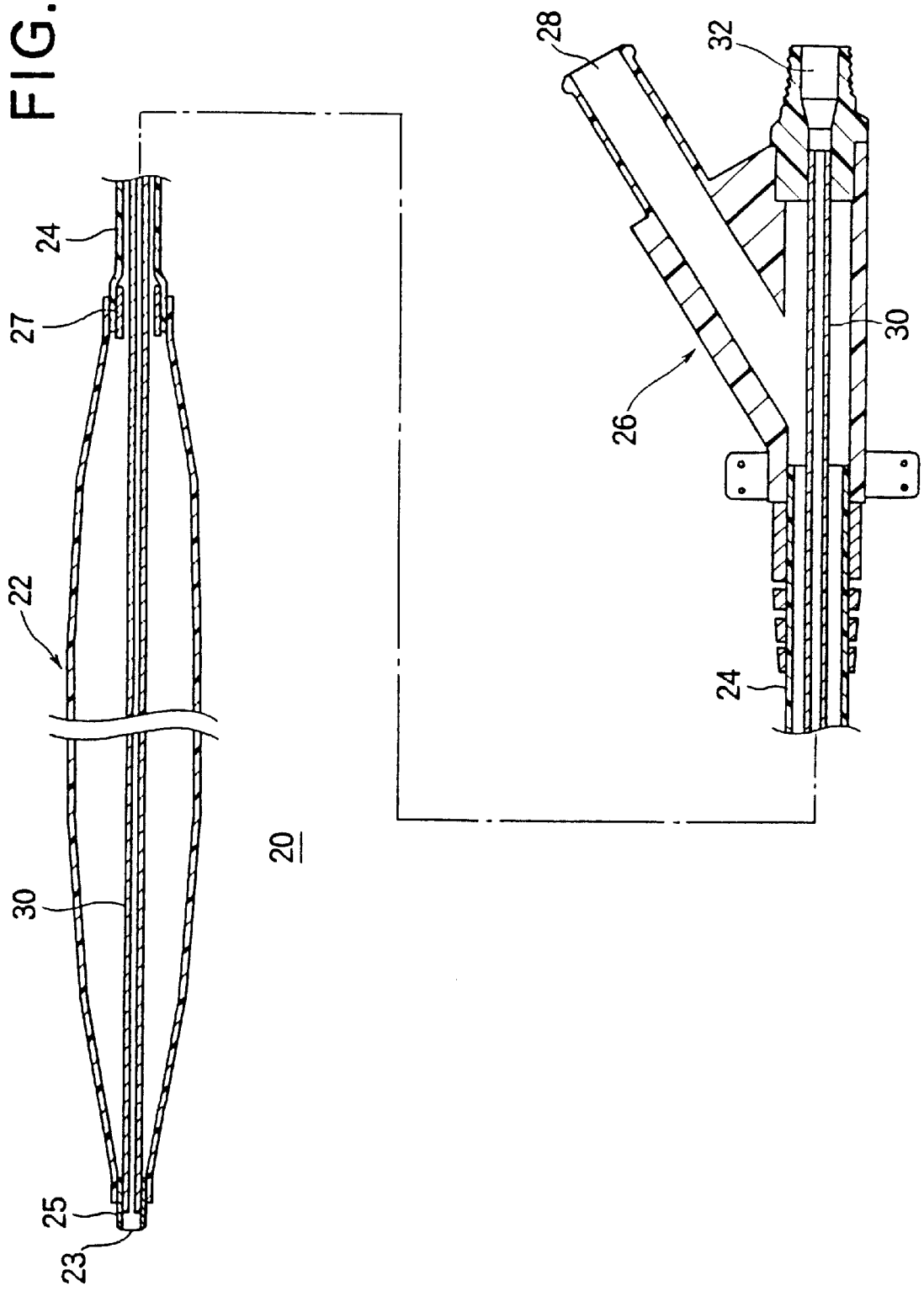
FIG. 4 is a cross-sectional view of a balloon catheter.

FIG. 4 illustrates the balloon catheter 20 for IABP in a cross-sectional view. The balloon 22 is formed of a cylindrical balloon film having a thickness of about 60 $\mu$m to 150 $\mu$m, and is expanded and deflated in agreement with the heart beat of the patient. In the first embodiment, the balloon is cylindrical when it is expanded. However, it may have the shape of a polygonal column.

The balloon 22 is made of an anti-fatigue material having a superior bend-resistance. The outer diameter and the length of the balloon 22 are determined according to the volume of the balloon 22, which greatly influences the medical effect on the heart function, and the inner diameter of the artery. In general, the volume of the balloon 22 is 30 cc to 50 cc, the expanded outer diameter is 14 mm to 16 mm, and the length is 210 mm to 270 mm.

The distal end of the balloon 22 is fixed to the outer face of the distal end of the inner tube 30 directly, or via a short tube 25, by thermal fusion or mechanical adhesion.

The other end of the balloon 22 is fixed to the proximal end of the catheter tube 24 directly or via a radiopaque marker, such as a metal tube 27. A pressurized gas is introduced into and sucked out of the balloon 22 through the first lumen formed inside the catheter tube 24, thereby inflating and deflating the balloon 22. The balloon 22 and the catheter tube 24 are connected to each other by thermal fusion or an adhesive, such as a ultraviolet-curing resin.

The inner tube 30 is inserted into the catheter tube 24, and the distal end of the inner tube 30 extends from the distal end of the catheter tube 24 through the balloon 22 along the axial direction. The proximal end of the inner tube 30 is connected to the second port 32 of the bifurcation 26. A second lumen is formed inside the inner tube 30. The second lumen does not communicate with the first lumen formed inside the catheter tube 24 and the balloon 22. The inner tube 30 receives the blood pressure at the opening 23 of the remote end, and transmits the blood pressure to the second port 32 of the bifurcation 26, through which the change in the blood pressure is measured.

When the balloon catheter 20 is inserted into the artery, the second lumen formed in the inner tube 30 functions as a guide wire introducing lumen for appropriately introducing the balloon 22 in the artery. When inserting the balloon catheter 20 into cavities, including a blood vessel, the balloon 22 is folded around the outer face of the inner tube 30. The inner tube 30 shown in FIG. 4 is formed of the same material as the catheter tube 24. The inner diameter of the inner tube 30 is not limited to a specific size as long as the guide wire can penetrate through it. For example, it is set to 0.15 mm to 1.5 mm, and the more preferable range is from 0.5 mm to 1.0 mm. Preferably, the thickness of the inner tube 30 is 0.1 mm to 0.4 mm. The length of the inner tube 30 is determined according to the length of the balloon catheter 20 which is to be inserted into the blood vessel, and it is generally set to 500 mm to 1200 mm, and more preferably to 700 mm to 1000 mm.

The catheter tube 24 is preferably made of a plastic material. Preferably, the inner diameter of the catheter tube 24 is 1.5 mm to 4.0 mm, and the thickness of the catheter tube 24 is 0.05 mm to 0.4 mm. The length of the catheter tube 24 is 300 to 800.

The proximal end of the catheter 24 is connected to the bifurcation 26 which is set outside the patient's body. The bifurcation 26 is formed separately from the catheter tube 24, and is connected to the catheter tube 24 by thermal fusion or mechanical adhesion. A first port 28, for inletting and outletting the shuttle gas in and from the first lumen of the catheter tube 24 and the balloon 22, and a second port 32, connected to the second lumen of the inner tube 30, are formed in the bifurcation 26.

Figure 5:
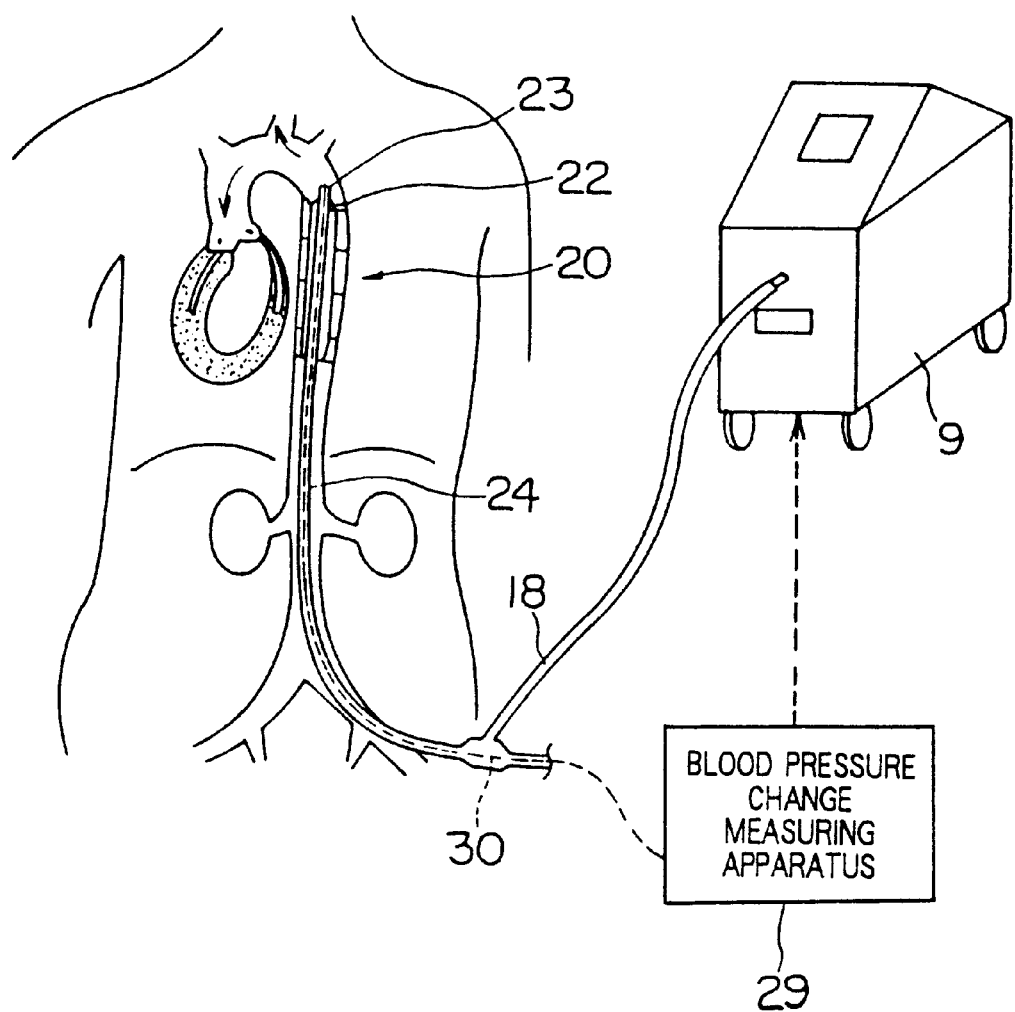
FIG. 5 is a cross-sectional view showing the balloon catheter in actual use.

The first port 28 is connected to the medical appliance driving apparatus 9 which has a structure, for example, as shown in FIG. 5. The medical appliance driving apparatus 9 supplies the shuttle gas into the balloon 22, and draws the gas out of the balloon 22. Many types of shuttle gas can be used to drive the balloon 22, but helium gas, which has a small viscosity and a small mass, is preferable because it allows the balloon 22 to expand and contract very quickly in response to the driving cycle of the apparatus 9.

The detailed structure of the apparatus 9 will be described later with reference to FIG. 1.

The second port 32 (FIG. 4) is connected to the blood-pressure measuring apparatus 29 shown in FIG. 5, whereby the blood pressure in the artery received at the aperture 23 of the distal end of the balloon 22 is supplied to the blood-pressure measuring apparatus 29. Based on the blood pressure detected by the measuring apparatus 29, the pump 9 is controlled in agreement with the heart beat of the patient so as to inflate and deflate the balloon 22 in a short cycle of 0.4 second to 1 second.

Figure 3:
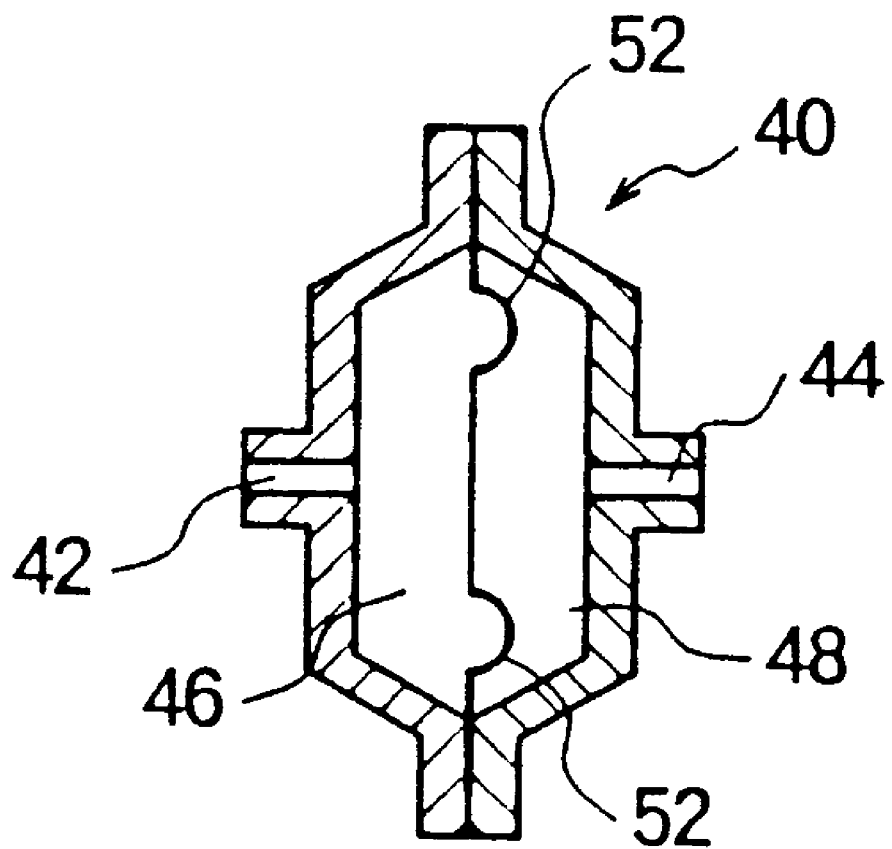
FIG. 3 is a cross-sectional view of a pressure-transfer partition.

In the balloon catheter 20 for IABP, helium gas is preferably used as the fluid for driving the balloon 22 because of its small mass and high response. Producing positive and negative pressure in the helium gas directly by the pump or a compressor is not economical because a portion of the generated pressure may be lost due to, for example, leakage from the sealed area. In order to avoid waste, the driving apparatus of the present invention employs the structure shown in FIG. 1, in which the secondary tube line 18 connected to the balloon 22, and the primary tube line 17 connected to the pump 4 (i.e., the primary pressure generator) are separated by the pressure-transfer isolator 40. An example of a pressure-transfer isolator 40 is shown in FIG. 3. This pressure-transfer isolator 40 has a first chamber 46 and a second chamber 48, which are partitioned by a diaphragm 52 in a sealed manner.

The first chamber 46 is connected to the primary tube line 17 via the port 42, while the second chamber 48 is connected to the secondary tube line 18 via the port 44. Although the fluid flow is shut off between the first chamber 46 and the second chamber 48, a pressure change (or a volume change) in the first chamber 46 is transferred to the second chamber 48 via the displacement of the diaphragm 52, and that pressure change appears in the second chamber 48 as a pressure change or a volume change in the second chamber 48. This arrangement allows any pressure changes in the primary tube line 17 to be transferred to the secondary tube line 18 without connecting these two tube lines.

In this embodiment, the primary tube line 17 is filled with air, and the secondary tube line 18 is filled with helium gas.

As shown in FIG. 1, a pump (i.e., a pressure generator) 4 is provided in the primary tube line 17. The positive output port of the pump 4 is connected to the first pressure tank (or the positive pressure tank), and the negative output port of the pump 4 is connected to the second pressure tank (or the negative pressure tank) 3.

The first and second pressure tanks 2 and 3 are furnished with pressure sensors 5 and 6, respectively, for detecting the inside pressure. The pressure data detected by the sensors 5 and 6 are supplied to the controller 10 respectively. The first and second pressure tanks 2 and 3 are also connected to the input ports of the first and second solenoid valves 7 and 8, respectively. The output ports of the first and second solenoid valves 7 and 8 are always open to the atmosphere. The solenoid valves 7 and 8 connect their input ports to the corresponding output ports in response to the output signal from the controller 10, whereby the inside pressure of the tanks 2 and 3 are open to the atmosphere at an appropriate time. The positions where the solenoid valves 7 and 8 are provided are not necessarily in the tanks 2 and 3. The solenoid valves 7 and 8 may be provided to the tubes near the pressure tanks 2 and 3. Furthermore, any type of valves, other than the solenoid valves, may be used.

The output port of the first (positive) pressure tank 2 is connected to the input port of the third solenoid valve 11, while the output port of the second (negative) pressure tank 3 is connected to the input port of the fourth solenoid valve 12. The switching of these solenoid valves 11 and 12 is controlled by the controller 10. The output ports of the third and fourth solenoid valves 11 and 12 are connected to the input port 42 (FIG. 3) of the pressure-transfer isolator 40.

As shown in FIG. 1, the driving apparatus has a third pressure sensor 15 for detecting the inside pressure of the secondary tube line 18, an solenoid valve 16 for evacuating the secondary tube line 18 prior to supplying helium gas into this line, and a gas supply system 60 for filling the secondary tube line 18 with a constant amount of helium gas. Since these elements are not directly related to the first embodiment, the explanation thereof will be omitted.

In the first embodiment, the inside pressure PT1 of the first pressure tank 2 is set to about 300 mm Hg (gauged pressure), and the inside pressure PT2 of the second pressure tank 3 is set to about −150 mm Hg (gauged pressure). The pressure applied to the input port of the pressure-transfer isolator 40 is converted to the pressures to be applied to the first and second pressure tanks 2 and 3 by alternately driving the solenoid valves 11 and 12. The timing of the switching between the solenoid valves 11 and 12 is controlled by the controller 10 synchronized with the heart beat of the patient.

Figure 2:
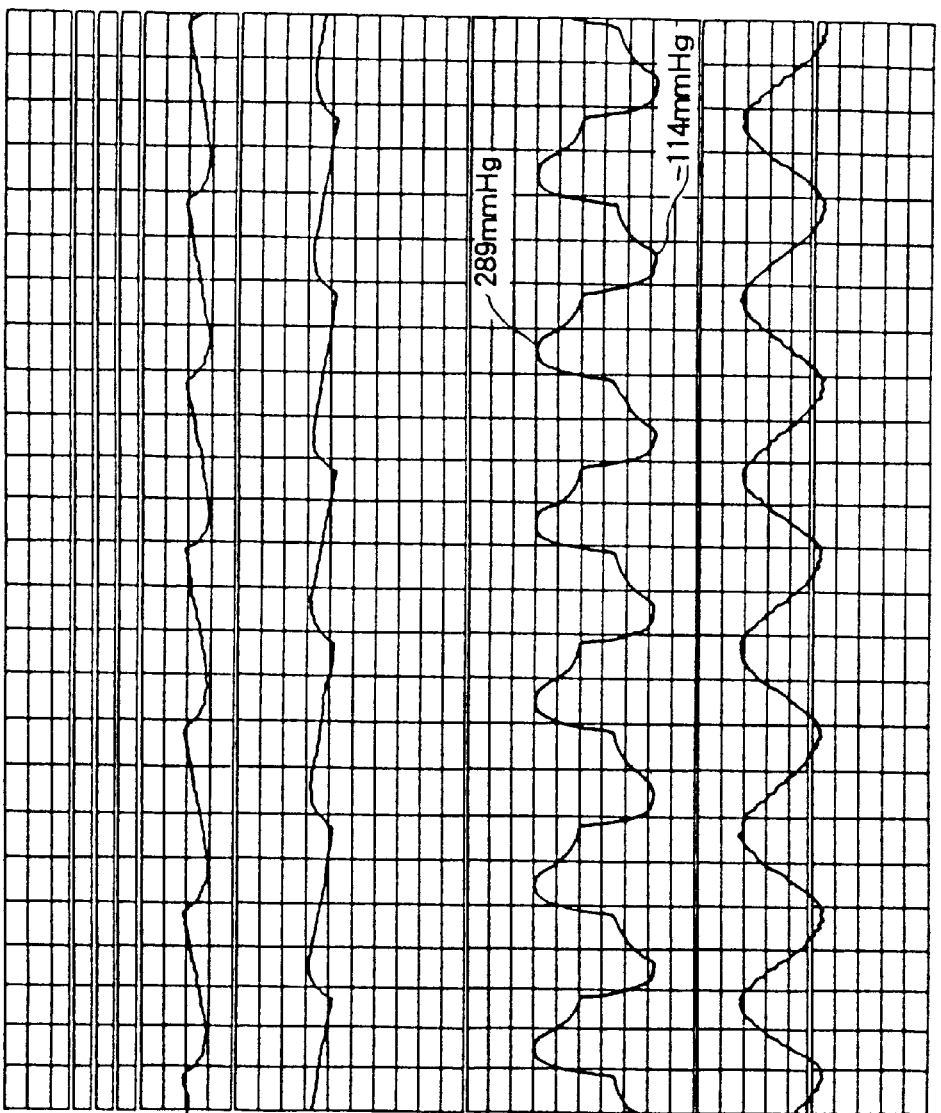
FIG. 2A is a graph showing the pressure changes in the respective pressure tanks.
FIG. 2B is a graph showing the pressure change in the balloon.
FIG. 2C is a graph showing the volume change of the balloon.

FIG. 2A shows the fluctuation of the pressures PT1 and PT2 detected by the sensors 5 and 6, and FIG. 2B shows the pressure PT3 generated in the secondary tube line 18 as a result of switching the solenoid valves 11 and 12. The change in pressure represented by pressure PT3 is detected by the pressure sensor 15. The peak pressure of the secondary tube line 18 is 289 mm Hg (gauged pressure), and the minimum is −114 mm Hg (gauged pressure). The pressure change in the secondary tube line 18 causes the volume of the balloon 22 to change as shown in FIG. 2C. In this manner, the balloon 22 inflates and deflates synchronized with the heart beat of the patient in order to support or assist the heart function of the patient.

The operation of the controller 10 will now be explained with reference to FIG. 6.

In step S1, the pressure sensors 5 and 6 read the inside pressure PT1 and PT2 of the first and second pressure tanks 2 and 3. Since the pressure PT1 and PT2 vary, as shown in FIG. 2A, the mean pressures PT1' and PT2' are obtained every predetermined period of time, for example, every 0.5 seconds to 3 seconds.

In step S2, the mean value Pa of the pressure data of the two tanks 2 and 3 is calculated based on the equation: Pa=(PT1'+PT2')/2. Then, in step S3, the pressure difference Pb between the mean pressures PT1' and PT2' of the two tanks is calculated based on the equation: Pb=(PT1'−PT2'). Note that the mean value Pa designates the intermediate value between the pressure data PT1' (positive number) and PT2' (negative number). The pressure difference Pb designates the width (or distance) between the pressure data PT1' and PT2'.

In step S4, it is determined if the calculated mean value Pa is greater than the predetermined mean value Pa'+α. The predetermined mean value Pa' is the mean value of the predetermined pressure data of the first and second tanks 2 and 3, and α is the error range which is set to, for example, 0 mm Hg to 30 mm Hg. If the calculated mean value Pa is greater than the predetermined mean value Pa'+α, it is regarded that the inside pressure of the first (positive) tank 2 is too high, and the process proceeds to step S5, in which the solenoid valve 7 (FIG. 1) is driven so that the first (positive) tank 2 is open to the atmosphere for a predetermined time to lower the inside pressure PT1, thereby bringing the calculated mean value Pa down to the predetermined mean value Pa'. The time period for opening the first tank 2 to the atmosphere is, for example, 5 ms to 50 ms.

If, in step S4, it is determined if the calculated mean value Pa is smaller than the predetermined mean value Pa'+α, the process proceeds to step S6, in which the calculated mean value Pa is then compared with the predetermined mean value Pa'−α. If the calculated mean value Pa is smaller than the predetermined mean value Pa'−α when compared in step S6, it is regarded that the inside pressure of the second (negative) tank 3 is too low, and the process proceeds to step S7. In step S7, the solenoid valve 8 (FIG. 1) is driven so that the second (negative) tank 3 is open to the atmosphere for a predetermined time to raise the inside pressure PT2, thereby bringing the calculated mean value Pa up to the predetermined mean value Pa'. The time period for opening the second tank 3 to the atmosphere may be the same as or different from the opening period of the first tank 2.

If the calculated mean value Pa lies within the range of predetermined mean values Pa'±α, it is not necessary to open the first tank 2 or second tank 3 and, accordingly, steps S5 and S7 are skipped. In this case, the process jumps to step S8. Steps S5 and S7 are also followed by step S8 when the calculated mean value Pa is out of the range predetermined mean value Pa'±α.

In step S8, it is determined if the detected pressure difference Pb is greater than the predetermined pressure difference value Pb'+β. The predetermined pressure difference value Pb' is the difference between the designated pressure data of the first and second pressure tanks 2 and 3, and β is the error range which is set to, for example, 0 mm Hg to 30 mm Hg. If the detected pressure difference Pb is greater than the predetermined difference value Pb'+β, it is regarded that the output level of the pump 4 is too high. In this case, the process proceeds to step S9, in which the output level of the pump 4 is lowered by, for example, adjusting the rotation number of the pump 4 on the basis of output signals from the controller 10 (FIG. 1) so that the detected pressure difference Pb approaches the predetermined difference pressure value Pb'.

If it is determined that the detected pressure difference Pb is smaller than the predetermined difference valve Pb'+β, the process proceeds to step S10, in which the detected pressure difference Pb is then compared with the predetermined pressure difference valve Pb'−β. If the detected pressure difference Pb is smaller than the predetermined difference valve Pb'−β in when compared in step S10, it is regarded that the output level of the pump 4 is too low. In this case, the process proceeds to step S11, and the output level of the pump 4 is raised by, for example, adjusting the rotation speed of the pump 4 on the basis of output signals from the controller 10 so that the detected pressure difference Pb approaches the predetermined pressure difference value Pb'.

In order to control the pump output, if the pump (e.g., a rotary pump, a diaphragm pump, a piston pump, etc.) has an AC induction motor, the output level of the pump can be lowered by decreasing the power source frequency or the amplitude of the power source voltage supplied to the AC induction motor. For a linear piston pump using an AC power source, the output level can be lowered by the same method. If the motor of the pump, such as a rotary pump, a diaphragm pump, a piston pump, etc., uses an servo-motor, the output level of the pump can be controlled by adjusting the target rotation speed. If the pump has a DC motor, the output level of the pump is controlled by regulating the PWM (pulse width modulation) of the motor power source or adjusting the exciting voltage/current.

If the detected pressure difference Pb lies within the range of the predetermined difference valve Pb'±β, the inside pressures PT1 and PT2 of the first and second pressure tanks 2 and 3 are kept at or near the predetermined pressure respectively, and the balloon 22 is satisfactorily inflated and deflated via the solenoid valves 11 and 12, and the pressure-transfer isolator 40. In this case, the process returns to step S1 from S10, and the same operations are repeated. The process also returns to step S1 from steps S9 and S11 in order to repeat the same operations.

In this manner, the pressures of the positive and negative tanks 2 and 3 are always monitored and regulated so as not to deviate from the acceptable range and, accordingly, the solenoid valves 7 and 8 are rarely opened. Thus, inlet and outlet of the gas flowing in the sealed circuit is kept minimum, and the wasteful work abandoned outside is greatly eliminated. This, together with the stable pump output, can reduce the total power consumption and improve the energy efficiency.

It should be understood that the present invention is not limited to this specific example, and that many changes can be made within the scope of the invention.

For example, a diaphragm pump is used as the pump (or the pressure generator) 4 in this first embodiment. However, many other pumps, such as a linear piston pump, a rotary vane pump, a piston pump, a compressor, or similar can be used.

Although, in the first embodiment, two solenoid valves (i.e., the third and fourth valves) 11 and 12 are used as the pressure switching means, a three-way valve may be used to switch the pressure applied to the input port of the pressure-transfer isolator 40.

Figure 6:
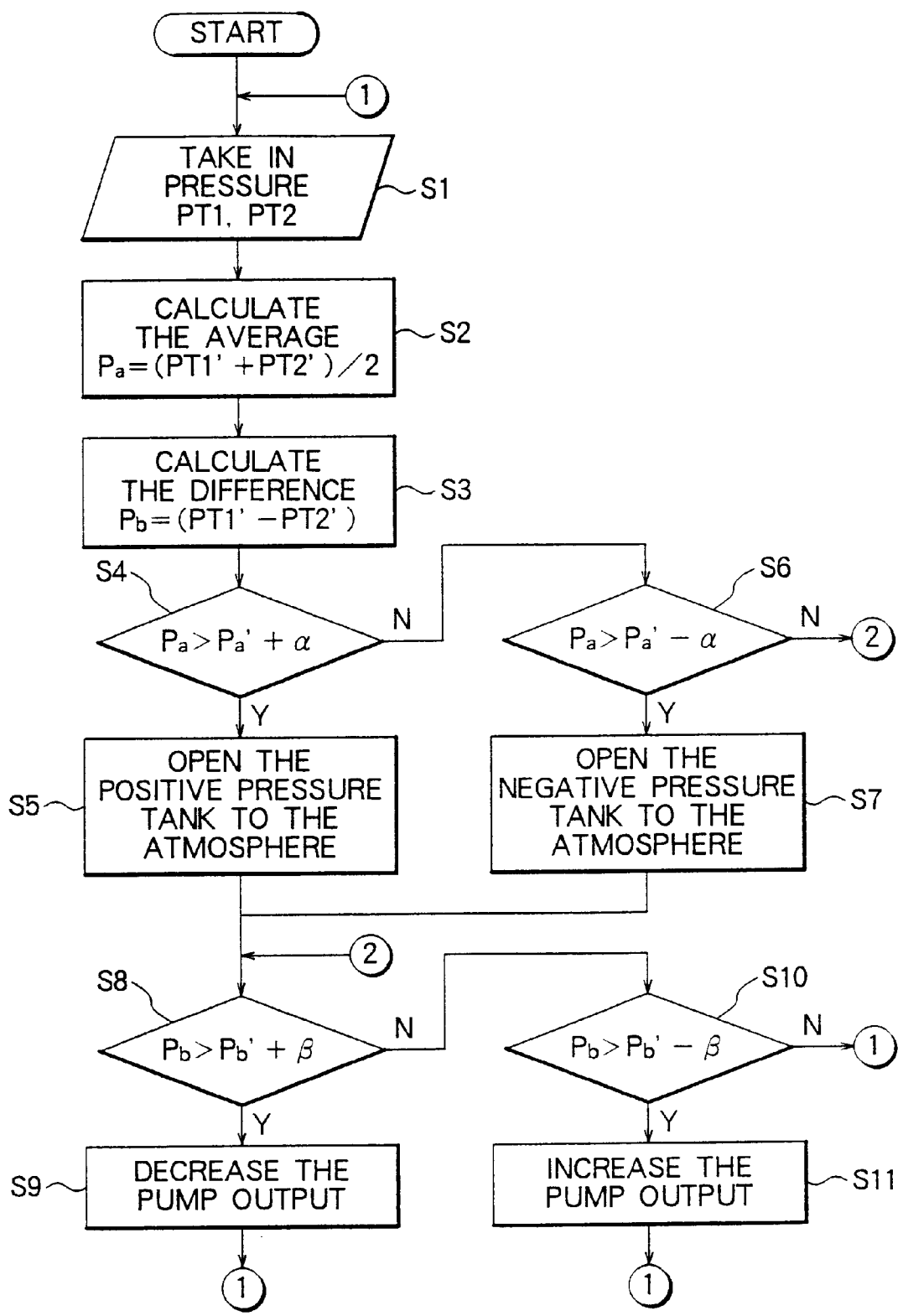
FIG. 6 is a flow chart showing the operation flow of the controller.

In the flowchart shown in FIG. 6, two different control operations (one comprising steps S1, S2 and S4 through S7, the other comprising steps S1, S3 and S8 through S11) are performed in series. However, only one of them may be performed.

The gas flowing through the first tube line 17 is not limited to air, and other fluid may be used in place of the air. Similarly, the gas flowing through the second tube line 18 is not limited to helium gas.

The first tube line 17 can be connected directly to a medical appliance, such as an artificial heart, in order to directly drive the medical appliance.

In the first embodiment, helium gas is supplied by the gas supply system 60 shown in FIG. 1, explanation of which is omitted because any known type of gas supply systems can be used. The means for evacuating the second tube line prior to the actual driving is not shown in the drawings.

(Second Embodiment)

Figure 7:
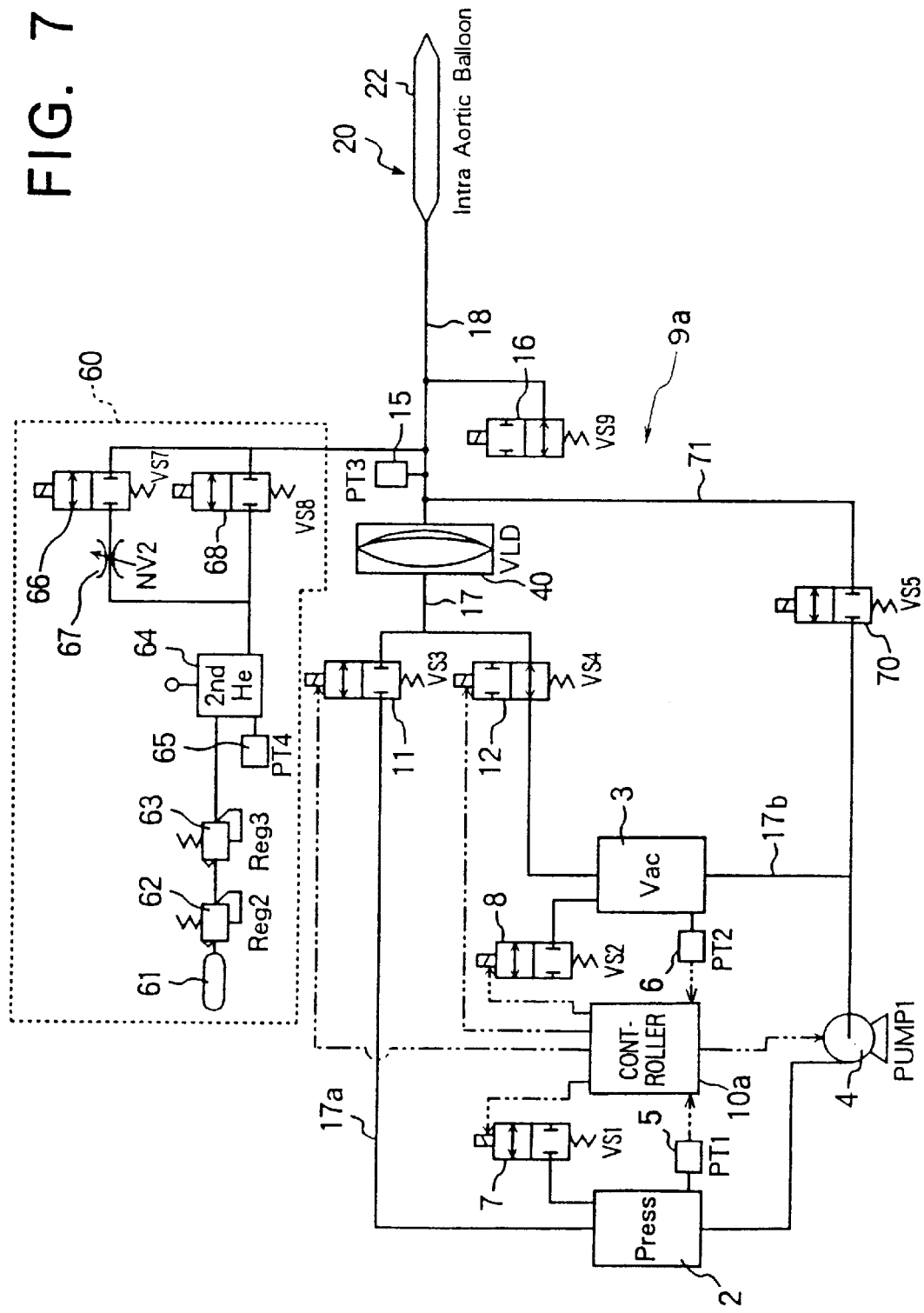
FIG. 7 is a schematic diagram of the medical-appliance driving apparatus according to the second embodiment of the present invention.

FIG. 7 illustrate the medical-appliance driving apparatus 9a according to the second embodiment. This driving apparatus is a modification of the driving apparatus 9 shown in FIG. 1, and the same elements are denoted by the same numerical symbols as those shown in FIG. 1.

In the second embodiment, a single pump 4 is provided in the first tube line 17, and it is used as a primary side pressure generator. The pump 4 is, for example, a diaphragm pump with its output variable.

A first pressure tank 2, which serves as a positive pressure tank, is connected to the positive-pressure output port of the pump 4, while a second pressure tank 3, which serves as a negative pressure tank, is connected to the negative-pressure output port of the pump 4. The primary tube line 17 comprises a positive line 17a, connected to the first pressure tank 2, and a negative line connected to the second pressure tank 3.

The first and second pressure tanks 2 and 3 are provided with pressure sensors 5 and 6 for detecting the inside pressure of these tanks. The detection signals generated by the pressure sensors 5 and 6 are supplied to the controller 10a. The pressure tanks 2 and 3 are connected to the input ports of the first and second solenoid valves 7 and 8. The output ports of the first and second solenoid valves 7 and 8 are open to the atmosphere. The input ports of the solenoid valves 7 and 8 are connected to their output ports at a desired timing according to the signal level supplied from the controller 10a. By connecting the input and output ports of each of the solenoid valves 7 and 8, either of the tanks 2 or 3 may be opened to the atmosphere. The solenoid valves 7 and 8 may be provided directly to the pressure tanks 2 and 3, or alternatively, may be provided to the positive and negative lines 17a and 17b near the pressure tanks 2 and 3. The valves are not limited to solenoid valves, and any type of valves can be used.

The output port of the first pressure tank 2, which is connected to the positive line 17a of the primary tube line 17, is connected to the input port of the third solenoid valve 11, while the output port of the second tank 3, which is connected to the negative line 17b, is connected to the input port of the fourth solenoid valve 12. The timing for the opening and closing of the solenoid valves 11 and 12 is controlled by the controller 10a. The output ports of the solenoid valves 11 and 12 are connected to the input port 42 of the pressure-transfer isolator 40 as shown in FIG. 3.

The output port 44 of the pressure-transfer isolator 40 is connected to the secondary tube line 18 as shown in FIG. 7. The secondary tube line 18 is made of, for example, a hose or a tube, and is connected to the balloon 22. This secondary tube line 18 is a sealed line, in which helium gas is supplied when driving the balloon catheter 20. A pressure sensor 15 is provided to the secondary tube line 18 in order to detect the inside pressure of this line. The output of the pressure sensor 18 is supplied to the controller 10a.

An solenoid valve 16 is also provided to the secondary tube line 18. If the gas pressure inside the secondary tube line 18 exceeds a predetermined value, the solenoid valve 16 is opened for a predetermined time under the control of the controller 10a, thereby discharging a portion of the gas.

A gas supply system 60 is connected to the secondary tube line 18. The gas supply system 60 supplies a predetermined amount of helium gas to the secondary tube line 18 so that the chemical equivalent of the inside gas is always kept constant. The gas supply system 60 has a primary helium gas tank 61, which is connected to the secondary helium gas tank 64 via the regulator 62 and 63. A pressure sensor 65 is provided to the secondary helium gas tank 64. Based on the pressure detected by the pressure sensor 65, the inside pressure of the tank 64 is kept constant under the control of the controller 10a. The inside pressure of the tank 64 is set to, for example, 100 mm Hg or less.

A fill-up solenoid valve 66 and an initial charging solenoid valve 68 are connected in parallel and to the secondary helium tank 64 via a speed control valve 67. These solenoid valves 66 and 68 are controlled by the controller 10a. The initial charging solenoid valve 68 is used to initially charge the evacuated secondary tube line 18 with helium gas, and it opens in association with the pump 4 and the solenoid valve 70, which will be described below. The solenoid valve 68 is not activated after this initial charging step. Instead, the solenoid valve 66 is used in the normal operation to supply additional helium gas into the secondary tube line 18 for the purpose of compensating for leakage or diffusion of the inside gas.

In the second embodiment, a gas substitution tube line 71 is provided to connect the secondary tube line 18 and the negative line 17b of the primary tube line 17 in a disconnectable manner. An solenoid valve 70 is provided in the middle of the gas substitution tube line 71, and this valve 70 actually controls the connection and the disconnection between the secondary tube line 18 and the negative line 17b.

The secondary tube line 18 is evacuated via the gas substitution tube line 71 prior to driving the balloon catheter 20. The solenoid valve 70 is closed in normal operation. Then, the secondary tube line 18 is filled with helium gas. In the evacuation, the solenoid valve 70 is first opened in order to connect the secondary tube line 18 and the negative line 17b. At this time, the solenoid valve 7 is also open, while the other solenoid valves 8, 11, 12, 16, 66, and 68 are closed. In this state, the pump 4 is driven to suck the air output of the secondary tube line 18 to via the solenoid valve 7.

When the inside pressure of the secondary tube line 18 is adequately lowered, preferably lower than −500 mm Hg (gauged pressure), the initial charging solenoid valve 68 is opened to supply helium gas into the secondary tube line 18. At the same time, or after a second, the electromagnetic valve 70 is closed, and the pump 4 is stopped. The helium gas is supplied until the gas pressure of the secondary tube line 18 reaches, for example, +10±4 mm Hg (gauged pressure), for the balloon catheter 20 having a volume of 40 cc. If a balloon catheter 20 with a volume of 30 cc is used, then the charging gas pressure is set to −80±4 mm Hg (gauged pressure).

During the helium gas supply, the charging pressure in the secondary tube line 18 is monitored by the pressure an sensor 15. When the inside pressure of the secondary tube line 18 reaches predetermined pressure, the solenoid valve 68 is closed. Because the molecular weight of helium gas is small and, accordingly, it can easily escape through the walls of the balloon and the tube line, helium gas must be supplied appropriately to the secondary tube line 18 while the balloon catheter 20 is being used. If shortage of the helium gas is detected by the pressure sensor 15, the solenoid valve 66 is opened several times in a certain duration in order to supply additional helium gas.

In regular operation, the pump 4 is driven, while the solenoid valve 70 is closed, to bring the pressure PT1 of the first pressure tank 2 to about 300 mm Hg (gauged pressure) and to bring the pressure PT2 of the second pressure tank 3 to about −150 mm Hg (gauged pressure). The pressure applied to the input port of the pressure-transfer isolator 40, as shown in FIG. 7, is switched between PT1 and PT2 of the first and second pressure tanks 2 and 3, respectively by alternately driving the solenoid valve 11 and 12, respectively. The switching timing is controlled by the controller 10a so as to be synchronizes with the heart beat of the patient.

FIG. 2A is a graph showing the pressures PT1 and PT2 continuously detected by the pressure sensors 5 and 6, respectively. FIG. 2B shows the pressure PT3 produced in the secondary tube line 18 as a result of alternately opening the pressures tanks 2 and 3 using the solenoid valves 11 and 12, respectively. The pressure PT3 is detected by the pressure sensor 15. The peak pressure of the secondary tube line 18 is 289 mm Hg (gauged pressure) in this example, and the minimum pressure is −114 mm Hg (gauged pressure). The pulse-like pressure PT3 in the secondary tube line 18 causes the volume of the balloon 22 to change as shown in FIG. 2C. In consequence, the balloon 22 inflates and deflates in synchronized with the heart beat of the patient, thereby assisting the heart function of the patient.

The operation of the controller 10a, for simultaneously generating positive and negative pressure using a single pump 4, is the same as that in the first embodiment, and the explanation thereof will be omitted here.

As in the first embodiment, the solenoid valves 7 and 8 are rarely opened during normal operation. Accordingly, the inlet/outlet amount of the gas flowing through the sealed circuit (i.e., the primary tube line 17) is kept to a minimum, while the amount of work abandoned to the outside is greatly reduced. As a result, the power consumption is reduced by well regulating the pump output, and the energy efficiency is improved.

A single pump is used not only to generate positive and negative pressures in the primary tube line 17, but also to evacuate the secondary tube line 18 prior to supplying helium gas to drive the balloon catheter 20. This arrangement can reduce the size and weight of the driving apparatus, while the reliability is kept high.

(Third Embodiment)

Figure 8:
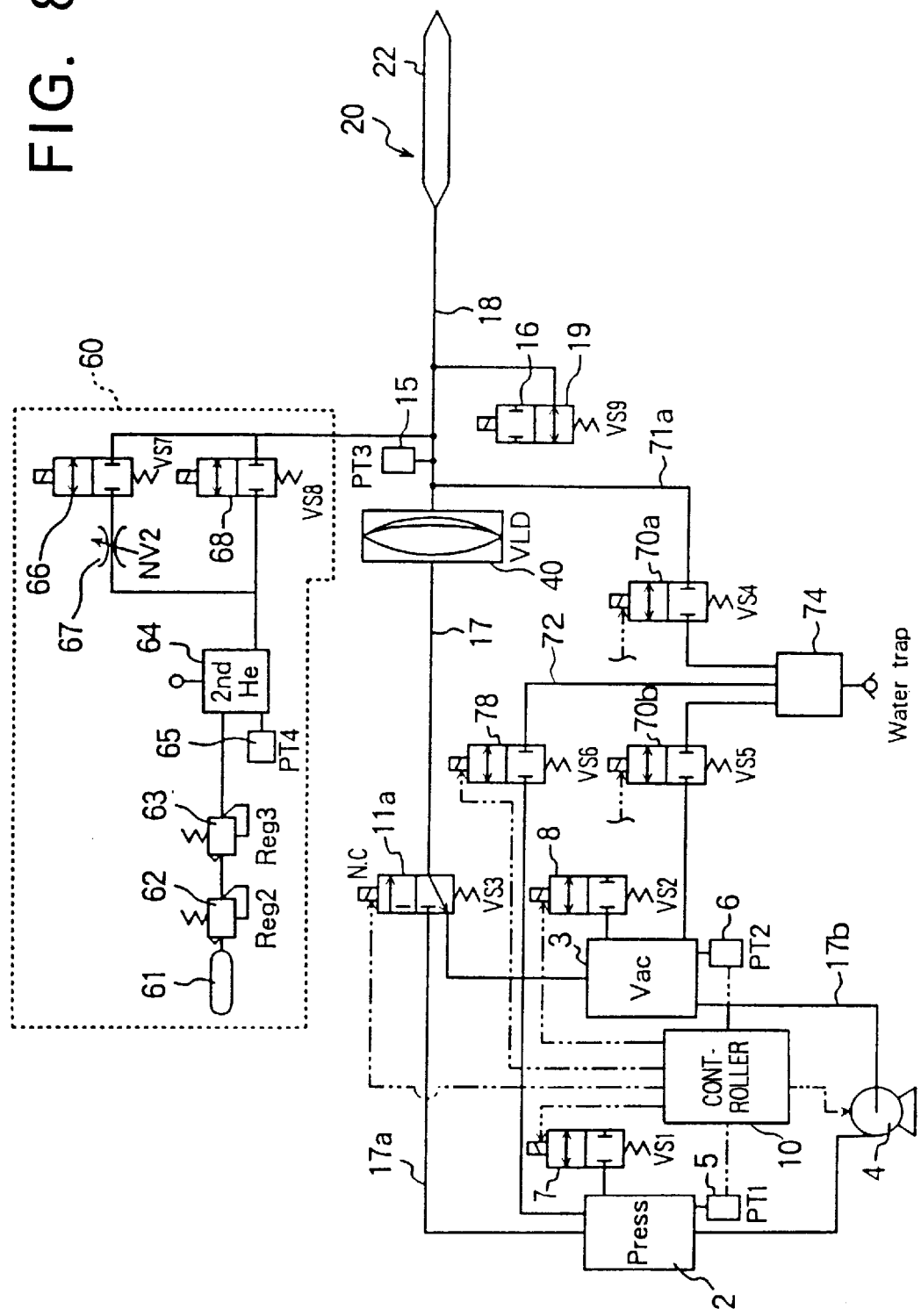
FIG. 8 is a schematic diagram of the medical-appliance driving apparatus according to a third embodiment of the present invention.

FIG. 8 shows the medical-appliance driving apparatus 9b according to the third embodiment of the present invention, which is a modification of the driving apparatus 9a shown in FIG. 7. The numerical symbols denote the same element as those shown in FIG. 7.

The driving apparatus of the third embodiment uses a three-way solenoid valve 11a, in place of the two solenoid valves 11 and 12 as shown in FIG. 7, to switch between the positive line 17a and negative line 17b and supply one of the pressures to the pressure-transfer isolator 40.

The gas substitution tube line 71a is connected to the second tank 2 provided in the negative line 17b and to the secondary tube line 18. As a feature of the third embodiment, a water trap 74 is provided in the middle of the gas substitution tube line 71a, and solenoid valves 70a and 70b are provided on either side of the water trap 74.

A drain is formed in the water trap 74 in order to remove the moisture contained in the gas flowing through this tube line. The water trap 74 is connected to one end of the positive-pressure application tube line 72. The other end of the tube line 72 is connected to the first tank 2 provided in the positive line 17a. An solenoid valve 78 is provided in the midway of the positive-pressure application tube line 72 in order to control the connection and disconnection between the first tank 2 and the water trap 74.

Prior to using the balloon catheter 20, the secondary tube line 18 is evacuated and, then, filled with helium gas.

In the third embodiment, the solenoid valves 70a and 70b are first opened to connect the secondary tube line 18 to the second tank 3 in the negative line 17b. At this time, the solenoid valve 7 is also open, while the other solenoid valves 8, 16, 66, and 68 are closed. The solenoid valve 11a is set at this time to connect the line 17a to the pressure-transfer isolator 40. In this state, the negative line 17b is closed, and the pump 4 is driven to evacuate the secondary tube line 18. Thus, the air is discharged from the secondary tube line 18 to the atmosphere via the solenoid valve 7. When the pressure in the secondary tube line 18 is sufficiently reduced, the solenoid valves 70a and 70b are closed. During this process, moisture component contained in the gas is liquefied, and water drops accumulate in the water trap 74 through the secondary tube line 18 and the positive-pressure application line 71a. In order to remove the accumulated water, the solenoid valve 78 is opened to feed the positively pressurized air from the second tank 2 into the water trap 74, thereby forcibly outletting the water from the drain.

As in the second embodiment, when the inside pressure of the secondary tube line 18 is reduced to about −500 mm Hg (gauged pressure), the initial charging solenoid valve 68 is opened to supply the helium gas into the secondary tube line 18. At the same time or after a second, the solenoid valves 70a and 70b are closed, and the pump 4 is stopped. The fill-up pressure of the helium gas in the secondary tube line 18 is the same as in the second embodiment. The pressure is monitored by the pressure sensor 15, and when the fill-up pressure reaches the predetermined value, the solenoid valve 68 is closed.

As shown in FIG. 8, the same gas supply system 60 as in FIG. 7 is used to supply the helium gas, and the explanation thereof will be omitted here.

The water trap 74 located in the gas substitution line 71a can prevent water from entering the pump 4 and the primary tube line 17, which is connected to the pump 4 and the pressure tanks 2 and 3, during the gas substitution process prior to using the balloon catheter 20. If a moisture gets into the pump 4 and the primary tube line 17, the load on the pump 4 becomes too large, which may cause a malfunction.

In the third embodiment, positive pressure is applied to the water trap 74 from the positive pressure tank 2 of the positive line 17a, thereby forcibly draining the water from the water trap 74.

There are many modifications other than the second and third embodiments. In addition, the control operation is not limited to that as shown in FIG. 6.

The driving apparatuses described in the second and third embodiments can be applied to any medical appliances, other than balloon catheters, that repeat expansion and contraction.

(Fourth Embodiment)

The driving apparatus according to the fourth embodiment of the present invention is used to drive a balloon catheter 20 for IABP. The overall structure of the driving apparatus is the same as one of those shown in FIGS. 1, 7, and 8. Although a single pump 4 is used in the previous embodiments, two or more pumps may be used in the driving apparatus of the fourth embodiment.

Figure 9:
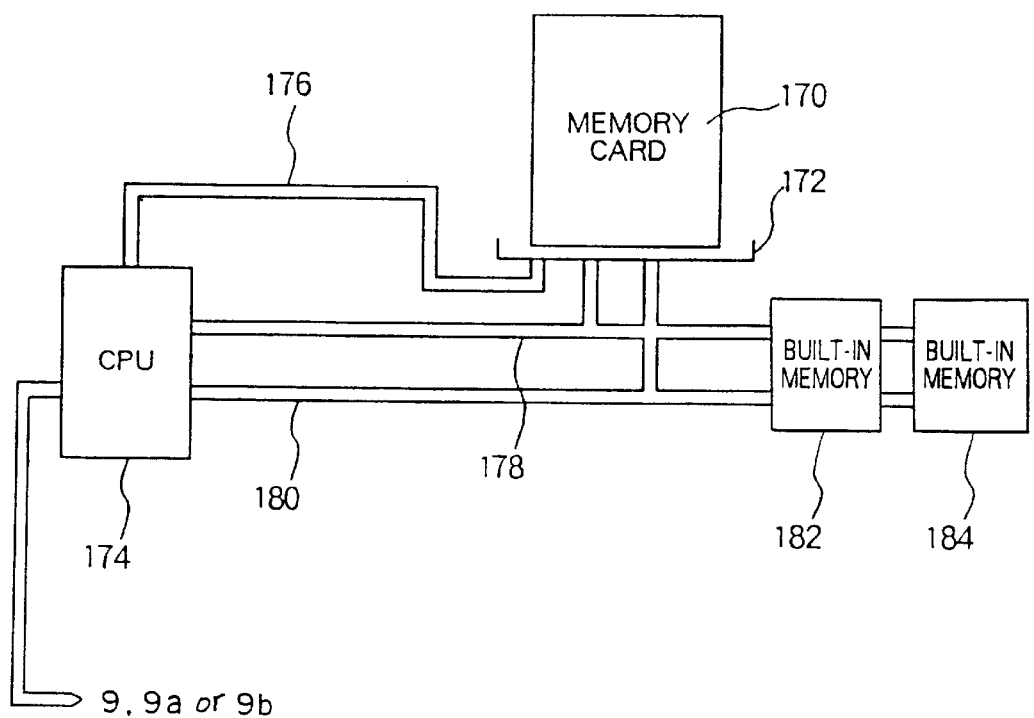
FIG. 9 shows the relationship between the data storage medium and the driving state monitor used in the IABP driving apparatus according to a fourth embodiment of the present invention.

As shown in FIG. 9, a memory card 170 is attached to the connector 172 in the driving apparatus. The memory card 170 is removable from the housing of the driving apparatus. The connector 172 is further connected to the central processing unit or CPU 174 via a control bus 176, an address bus 178, and a data bus 180. The CPU 174 serves both as a driving state monitor and a controller (e.g., the controller 10a as shown in FIG. 7). The CPU 174 controls the operations of the pump 4 and the solenoid valves 11, 12, 66, and 68 based on the detection signals supplied from the pressure sensors 5, 6, 15, 65 as shown in FIG. 7. A separate CPU for monitoring the driving state of the driving apparatus 9a may be provided to the driving apparatus 9a in addition to the CPU for controlling the driving apparatus 9a.

The CPU 174, shown in FIG. 9, is connected to the built-in memories 182 and 184 via the address bus 178 and the data bus 180. The built-in memory 182 and 184, as well as the memory card 170, are a part of the memory of the CPU 174, and are located in the memory area which is directly accessible by the CPU 174. In the fourth embodiment, a battery-back upped RAM conformable to the PCMCIA (Release 2.1) standard is used as the memory card 170.

The writing rate of the battery-back upped RAM is very high, and it takes only several tens to several hundreds of nanoseconds to write the data. The battery-back upped RAM stores the data as groups of variables in the memory without requiring a special writing process. Furthermore, a so-called active-line connection/disconnection is allowed to the battery-back upped RAM. This means that the memory card 170 can be connected to and disconnected from the connector 172, which is in the active state connected to the power source, without causing problems in the hardware.

Figure 10:
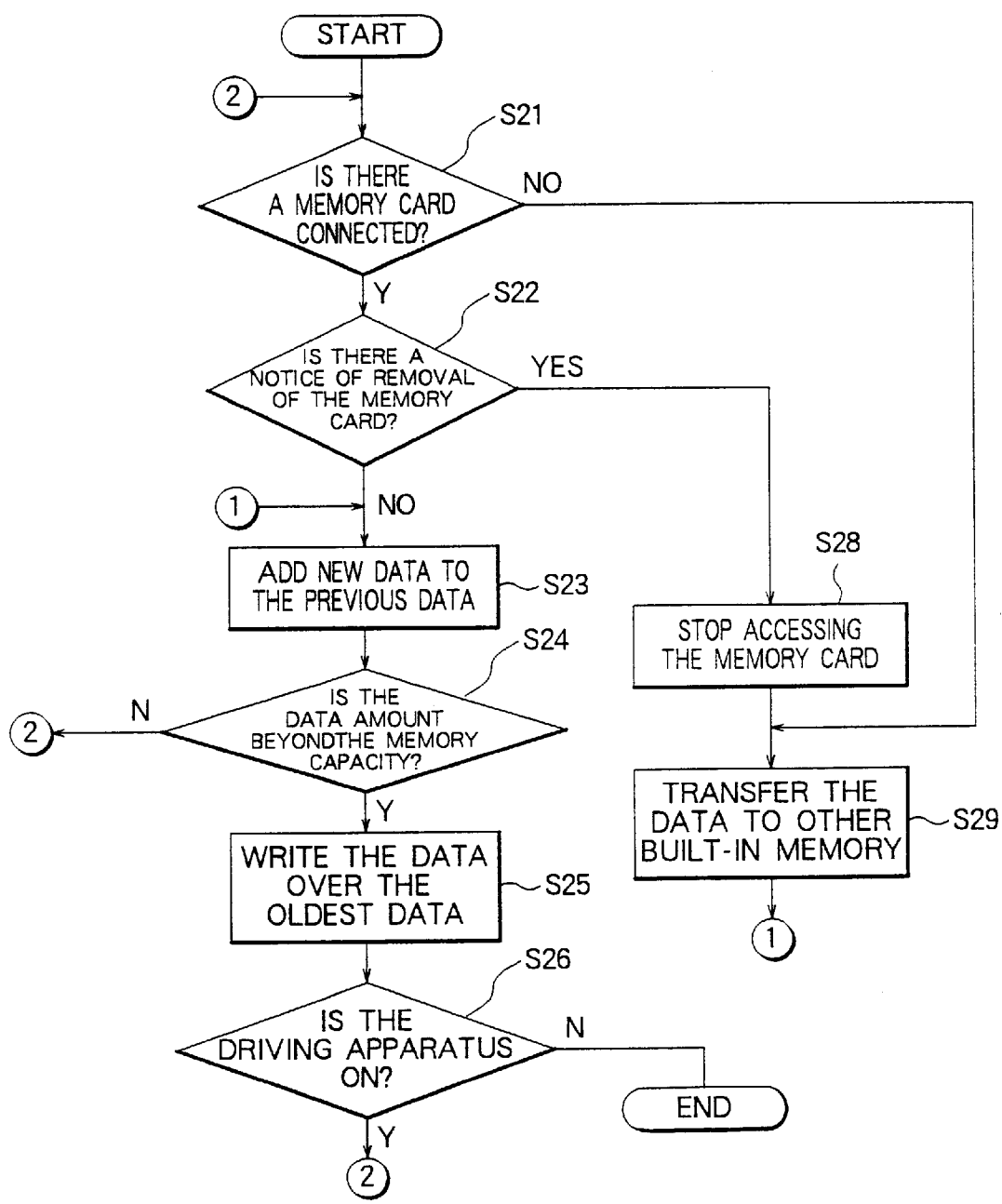
FIG. 10 is a flow chart showing the operation of the driving state monitor.

FIG. 10 shows the operation flow of the CPU 174 shown in FIG. 9.

First, in step S21, the CPU 174 accesses the memory card 170 via the control bus 176 in order to determine if the memory card 170 is connected to the connector 172. If the memory card 170 is connected to the connector 172, the process proceeds to step S22. If the memory card 170 is not connected to the connector 172, the process jumps to step S29, in which the CPU 174 stores the data described afterward in the built-in memories 182 and 184.

In step S22, it is determined if a signal representing a notice of removal of the memory card 170 has been received. This step is necessary because if the memory card 170 is removed from the connector 172 during the access of the CPU 174 to the memory card 170, a part of the data stored in the memory card 170 may be destroyed, and a malfunction may be caused in the CPU 174. If the notice signal has been received, the process proceeds to step S28, in which the CPU 174 stops accessing the memory card 170. Then, in step S29, the CPU 174 starts transferring the data to the built-in memories 182 and 184, instead of transferring the data to the memory card 170.

The operator who wishes to remove the memory card 170 from the driving apparatus simply hits a removal button provided on the driving apparatus. This removal button may be a contact-type or a non contact-type sensor. In this case, if the operator reaches his/her hand to the memory card 170, the sensor detects the approach of the hand, and it supplies a removal notice signal to the CPU 174.

If there is no removal notice signal received in step S22, the process proceeds to step S23, in which the CPU 174 accesses the memory card 170 and writes the driving state data of the driving apparatus 9a as groups of variables in the memory card 170. The current data is added to the stored previous data. The driving state data includes, but is not limited to, a blood pressure waveform measured by the blood pressure sensor 29 (FIG. 5) built in the driving apparatus, an electrocardiograph, the balloon driving pressure, the volume of the balloons as shown in FIGS. 2A through 2C, and alarm data indicating the abnormal operation of the gas supply system 60. In addition to these data, the operation time of the pump 4 (FIG. 4), the number of operations of the pressure-switching solenoid valves 11 and 12 and the gas-supply solenoid valves 66 and 68, the number an of charges/discharges of the battery, the power source voltage of each component, the internal temperature of the driving apparatus 9a, and other maintenance data can be stored in the memory card 170 in time series.

It is not necessary to continuously write the data. For example, the data is sampled for four seconds every ten minutes. This sampling and writing method allows the driving state data to be written in the memory card 170 for more than 10 hours in the normal operation.

It is preferable to employ a ring buffer method when writing the data, as shown in steps S24 and S25. That is, when the data amount exceeds the memory capacity of the memory card 170, the current data is written over the oldest data so that the latest data is always stored in the memory card 170.

Returning to step S29, if the memory card 170 is not connected to the connector 172 (FIG. 9), and if a removal notice signal is received by the CPU 174, then the data is written in the fixed type built-in memories 182 and 184 using the same writing method, instead of performing steps S23 through S25. If the memory card 170 is again inserted into the connector 172 of the driving apparatus 9a, the past driving state data stored in the built-in memories are transferred to the memory card 170.

In step S26, it is detected if the main switch of the driving apparatus 9a (FIG. 7) has been turned off. If so, the process terminates because it is not necessary to store the driving state any longer. As long as the main switch is ON, the process repeats from step S21.

In the fourth embodiment, it is not necessary to connect a personal computer directly to the driving apparatus 9a in order to analyze the data and, consequently, there is no danger of current leakage from the personal computer into the patient's body. The data stored in the memory card 170 can be transferred to an expert for data analysis via a telephone or by mail.

The memory card 170 does not require a special interface for the driving apparatus.

If an overwritable E2 PROM or a flash memory is used as the data storage medium, it takes several micro seconds ($\mu$s) to several millisecond (ms) to write data. In contrast, the memory card 170 comprising a battery-back upped RAM, can write the same amount of data much faster, (i.e., in several tens to several hundreds of nanoseconds). The battery-back upped RAM stores the data as groups of variables in the memory without requiring a special writing process in its program.

There are many modifications that can be made to the fourth embodiment. For example, two or more pumps may be used, instead of using a single pump 4 as shown in FIGS. 1, 7 and 8. In this case, a positive pressure pump is connected to the first positive pressure tank 2, and a negative pressure pump is connected to the second negative pressure pump 3.

A pressure generator for reciprocating a predetermined amount of gas directly to and from the driving tube line may be used in place of the primary tube line 17 and the pressure-transfer isolator 40 as shown in FIG. 7. Such a pressure generator comprises, for example, a bellows and a driving means from expanding and shortening the bellows along the axial direction. The inside or the outside of the pressure generator is connected directly to the driving tube line. By reciprocating the bellows in the axial direction using a motor, the gas can be reciprocated in the driving tube line at a predetermined time, thereby expanding and deflating the balloon. Preferably, the timing for driving of the motor to reciprocate the bellows is stored in the memory card 170.

Although a balloon catheter for IABP is driven by the driving apparatus in the fourth embodiment, this driving apparatus can be used to drive any medical appliances that are installed directly in or on the patient's body, such as an artificial heart.

ACTUAL EXAMPLES

Some examples of the present invention, together with some comparison examples, will be illustrated below. It should be noted that the present invention is not limited to these specific examples.

Example 1

A 40 cc balloon 22 was inflated and deflated at a driving rate of 150 beats/minute using the driving apparatus shown in FIG. 1. The solenoid valves 7 and 8, and the pump 4 were controlled based on the operation flow shown in FIG. 6. The power consumption was 70.8 W.

Example 2

The same balloon 22 was driven at a driving rate of 60 beats/minute using the same driving apparatus under the same control operation as example 1. The power consumption was 55.4 W.

Example 3

The same balloon 22 was driven at a driving rate of 150 beats/minute using the same driving apparatus as in example 1. In the control operation, only the pressure control of Pa=(PT1'+PT2')/2 was performed. Namely, the steps S1, S2, S4, S5, S6 and S7 of FIG. 6 were performed. The power consumption was 80.1 W.

Example 4

The same balloon 22 was driven at a driving rate of 60 beats/minute using the same driving apparatus as in example 1. In the control operation, only the pressure control of Pa=(PT1'+PT2')/2 was performed. Namely, the steps S1, S2, S4, S5, S6 and S7 of FIG. 6 were performed. The power consumption was 78.3 W.

Comparative Example 1

A 40 cc balloon 22 was inflated and deflated at a driving rate of 150 beats/minute using a single pump 4 as in Example 1. The control operation shown in FIG. 6 was not performed. Instead, when the inside pressure of the first pressure tank 2 (FIG. 1) exceeded the predetermined value, the first tank 2 was simply opened to the atmosphere for a predetermined time, and when the inside pressure of the second pressure tank 3 dropped below the predetermined value, the second tank 3 was simply opened to the atmosphere for a predetermined time. The power consumption was 91.2 W.

Comparative Example 2

The same balloon 22 was driven at a driving rate of 60 beats/minute under the same condition and the same control operation as Comparative Example 1. The power consumption was 89.4 W.

(Evaluation)

In Example 1, the power consumption was reduced by 20% as compared with Comparative Example 1. In Example 2, the power consumption was reduced by 40% as compared with Comparative Example 2.

Even in Examples 3 and 4, the power consumption could be reduced by 10% or more.

What is claimed is:

1. A medical-appliance driving apparatus comprising:
   a primary pressure generator for generating positive pressure and negative pressure at the same time, said pressure generator having a positive-pressure output port and a negative-pressure output port;
   a first pressure tank connected to said positive-pressure output port of said pressure generator;
   a first pressure sensor for detecting inside pressure of said first pressure tank;
   a first valve having an input port and an output port, said input port being connected to any one of said first pressure tank and a tube line near said first pressure tank, while said output port is open to the atmosphere;
   a second pressure tank connected to said negative-pressure output port of said pressure generator;
   a second pressure sensor for detecting inside pressure of said second pressure tank;
   a second valve having an input port and an output port, said input port being connected to any one of said second pressure tank and a tube line near said second pressure tank, while said output port is open to the atmosphere;
   a pressure switching means, connected to said first and second pressure tanks, for switching pressure between said first and second pressure tanks to output one of said pressure from an output port thereof; and
   a controller for controlling said first and second valves so that detection data detected by the first pressure sensor substantially equal to or more than first predetermined pressure data, and that detection data detected by said second pressure sensor substantially equal to or less than second predetermined pressure data.

2. A medical-appliance driving apparatus comprising:
   a primary pressure generator for generating positive pressure and negative pressure at the same time, said pressure generator having a positive-pressure output port and a negative-pressure output port;
   a first pressure tank connected to said positive-pressure output port of said pressure generator;
   a first pressure sensor for detecting inside pressure of said first pressure tank;
   a first valve having an input port and an output port, said input port being connected to any one of said first pressure tank and a tube line near said first pressure tank, while said output port is open to the atmosphere;
   a second pressure tank connected to said negative-pressure output port of said pressure generator;
   a second pressure sensor for detecting inside pressure of said second pressure tank;
   a second valve having an input port and an output port, said input port being connected to any one of said second pressure tank and a tube line near said second pressure tank, while said output port is open to the atmosphere;
   a pressure switching means, connected to said first and second pressure tanks, for switching pressure between said first and second pressure tanks to output one of said pressure from an output port thereof; and
   a controller for controlling said first and second valves so that detection data detected by the first pressure sensor substantially equal to or more than first predetermined pressure data, and that detection data detected by said second pressure sensor substantially equal to or less than second predetermined pressure data,
   wherein said controller calculates a mean value between said detection data detected by said first and second pressure sensors, and wherein if said mean value is greater than a predetermined mean value, said first valve is opened for a predetermined time, and if said mean value is smaller than said predetermined mean value, said second valve is opened for a predetermined time.

3. The medical-appliance driving apparatus according to any one of claims 1 and 2, wherein said controller calculates a pressure difference between said detection data detected by said first and second pressure sensors, and wherein if said pressure difference is greater than a predetermined difference value, an output level of said pressure generator is lowered, and if said pressure difference is smaller than said predetermined difference value, said output level of said pressure generator is raised.

4. The medical-appliance driving apparatus according to any one of claims 1 and 2, further comprising:
   a primary tube line having a positive-pressure line connected to said positive-pressure output port of said pressure generator, and a negative-pressure line connected to said negative-pressure output port of said pressure generator;
   a secondary side pressure generator comprising a pressure-transfer isolator, said pressure-transfer isolator having a first chamber, to which said positive pressure and said negative pressure generated by said primary pressure generator are alternately introduced via said primary tube line, and a second chamber isolated from said first chamber in a sealed manner, to which at least a portion of a pressure in said first chamber is transferred;
   a secondary tube line connected to said second chamber at a first end and to a device to be inflated and deflated by said driving apparatus at a second end;
   a gas substitution tube line connecting said secondary to tube line to said negative-pressure line of said primary tube line in a disconnectable manner; and
   a third valve, provided with said gas substitution tube line, for connecting and disconnecting said secondary tube line to and from said negative-pressure line of said primary tube line.

5. The medical-appliance driving apparatus according to claim 4, wherein a moisture remover is provided in said gas substitution tube line in order to remove any one of liquid and moisture contained in gas flowing through said gas substitution tube line.

6. The medical-appliance driving apparatus according to claim 5, wherein said positive pressure is applied to said moisture remover from said positive-pressure line of said primary tube line at an appropriate time, thereby forcibly removing any one of said liquid and said moisture using said positive pressure.

7. The medical-appliance driving apparatus according to any claim 1 or 2, further comprising:
   a driving state monitor for monitoring a driving state of said medical-appliance driving apparatus; and
   a data storage medium, attached to said driving apparatus in a detachable manner, for storing data representing said driving state monitored by said driving state monitor.

8. The medical-appliance driving apparatus according to claim 7, wherein said driving state monitor samples driving state data for predetermined duration at a predetermined time interval to produce sampled data, and stores said sampled data in said data storage medium in time series, and wherein if an amount of said sampled data exceeds a memory capacity of said data storage medium, current data is written over oldest data.

9. The medical-appliance driving apparatus according to claim 7, wherein when driving state monitor receives a signal representing a notice that said data storage medium is going to be removed from said driving apparatus, said driving state monitor stops transferring said data to said data storage medium and, instead, starts storing said data in other built-in storage media.

10. The medical-appliance driving apparatus according to any claim 1 or 2, wherein said medical-appliance driving apparatus is a driving apparatus for inflating and deflating a balloon catheter for IABP in synchronized with the heart beat of a patient.

11. The medical-appliance driving apparatus according to any one of claims 1 and 2, wherein said medical-appliance driving apparatus is a driving apparatus for driving an artificial heart.

12. A medical-appliance driving apparatus comprising:
a primary side pressure generator for generating positive pressure and negative pressure simultaneously, said primary side pressure generator having a positive-pressure output port and a negative-pressure output port;
a primary tube line having a positive-pressure line connected to said positive-pressure output port of said pressure generator, and a negative-pressure line connected to said negative-pressure output port of said pressure generator;
a secondary side pressure generator comprising a pressure-transfer isolator, said pressure-transfer isolator having a first chamber, to which said positive pressure and said negative pressure generated by said primary side pressure generator are alternately introduced via said primary tube line, and a second chamber isolated from said first chamber in a sealed manner, to which at least a portion of a pressure in said first chamber is transferred;
a secondary tube line connected to said second chamber at a first end and to a device to be inflated and deflated by said driving apparatus at a second end;
a gas substitution tube line for connecting said secondary tube line to said negative-pressure line of said primary tube line in a disconnectable manner; and
a valve, provided with said gas substitution tube line, for connecting and disconnecting said secondary tube line to and from said negative pressure line of said primary tube line.

13. The medical-appliance driving apparatus according to claim 12, wherein a moisture remover is provided in said gas substitution tube line in order to remove any one of a liquid component and a moisture component contained in gas flowing through said gas substitution tube line.

14. The medical-appliance driving apparatus according to claim 13, wherein said positive pressure is applied to said moisture remover from said positive-pressure line of said primary tube line at an appropriate time in order to forcibly remove any one of said liquid component and said moisture component using said positive pressure.

15. A medical-appliance driving apparatus comprising:
a primary pressure generator for generating positive pressure and negative pressure at the same time, said pressure generator having a positive-pressure output port and a negative-pressure output port;
a first pressure tank connected to said positive-pressure output port of said pressure generator;
a first pressure sensor for detecting inside pressure of said first pressure tank;
a first valve having an input port and an output port, said input port being connected to any one of said first pressure tank and a tube line near said first pressure tank, while said output port is open to the atmosphere;
a second pressure tank connected to said negative-pressure output port of said pressure generator;
a second pressure sensor for detecting inside pressure of said second pressure tank;
a second valve having an input port and an output port, said input port being connected to any one of said second pressure tank and a tube line near said second pressure tank, while said output port is open to the atmosphere;
a pressure switching means, connected to said first and second pressure tanks, for switching pressure between said first and second pressure tanks to output one of said pressure from an output port thereof; and
a controller for controlling said first and second valves so that detection data detected by the first pressure sensor substantially equal to or more than first predetermined pressure data, and that detection data detected by said second pressure sensor substantially equal to or less than second predetermined pressure data,
wherein said controller calculates a pressure difference between said detection data detected by said first and second pressure sensors, and wherein if said pressure difference is greater that a predetermined difference value, an output level of said pressure generator is lowered, and if said pressure difference is smaller than said predetermined difference value, said output level of said pressure generator is raised.

16. A medical-appliance driving apparatus comprising:
a primary pressure generator for generating positive pressure and negative pressure at the same time, said pressure generator having a positive-pressure output port and a negative-pressure output port;
a first pressure tank connected to said positive-pressure output port of said pressure generator;
a first pressure sensor for detecting inside pressure of said first pressure tank;
a first valve having an input port and an output port, said input port being connected to any one of said first pressure tank and a tube line near said first pressure tank, while said output port is open to the atmosphere;
a second pressure tank connected to said negative-pressure output port of said pressure generator;
a second pressure sensor for detecting inside pressure of said second pressure tank;
a second valve having an input port and an output port, said input port being connected to any one of said second pressure tank and a tube line near said second pressure tank, while said output port is open to the atmosphere;
a pressure switching means, connected to said first and second pressure tanks, for switching pressure between said first and second pressure tanks to output one of said pressure from an output port thereof;

a controller for controlling said first and second valves so that detection data detected by the first pressure sensor substantially equal to or more than first predetermined pressure data, and that detection data detected by said second pressure sensor substantially equal to or less than second predetermined pressure data;

a primary tube line having a positive-pressure line connected to said positive-pressure output port of said pressure generator, and a negative-pressure line connected to said negative-pressure output port of said pressure generator;

a secondary side pressure generator comprising a pressure-transfer isolator, said pressure-transfer isolator having a first chamber, to which said positive pressure and said negative pressure generated by said primary pressure generator are alternately introduced via said primary tube line, and a second chamber isolated from said first chamber in a sealed manner, to which at least a portion of a pressure in said first chamber is transferred;

a secondary tube line connected to said second chamber at a first end and to a device to be inflated and deflated by said driving apparatus at a second end;

a gas substitution tube line connecting said secondary tube line to said negative-pressure line of said primary tube line in a disconnectable manner; and a third valve, provided with said gas substitution tube line, for connecting and disconnecting said secondary tube line to and from said negative-pressure line of said primary tube line.

\* \* \* \* \*